US011786485B2

(12) United States Patent
Liu et al.

(10) Patent No.: US 11,786,485 B2
(45) Date of Patent: Oct. 17, 2023

(54) METHODS AND COMPOSITIONS FOR TREATING ADVANCED STAGE NON-SMALL CELL LUNG CANCER

(71) Applicant: Golden Biotechnology Corporation, Jersey City, NJ (US)

(72) Inventors: Sheng-Yung Liu, New Taipei (TW); Chih-Ming Chen, New Taipei (TW); Pei-Ni Chen, New Taipei (TW); Hao-Yu Cheng, New Taipei (TW)

(73) Assignee: Golden Biotechnology Corporation, Jersey City, NJ (US)

( * ) Notice: Subject to any disclaimer, the term of this patent is extended or adjusted under 35 U.S.C. 154(b) by 157 days.

(21) Appl. No.: 16/300,552

(22) PCT Filed: May 12, 2017

(86) PCT No.: PCT/US2017/032562
§ 371 (c)(1),
(2) Date: Nov. 10, 2018

(87) PCT Pub. No.: WO2017/197370
PCT Pub. Date: Nov. 16, 2017

(65) Prior Publication Data
US 2019/0209492 A1 Jul. 11, 2019

Related U.S. Application Data

(60) Provisional application No. 62/336,388, filed on May 13, 2016.

(51) Int. Cl.
| *A61K 31/122* | (2006.01) |
| *A61K 9/00* | (2006.01) |
| *A61P 35/00* | (2006.01) |
| *A61K 36/07* | (2006.01) |
| *A61K 9/48* | (2006.01) |
| *A61K 45/06* | (2006.01) |

(52) U.S. Cl.
CPC .......... *A61K 31/122* (2013.01); *A61K 9/0019* (2013.01); *A61K 9/4858* (2013.01); *A61K 9/4866* (2013.01); *A61K 36/07* (2013.01); *A61K 45/06* (2013.01); *A61P 35/00* (2018.01)

(58) Field of Classification Search
CPC .. A61K 31/122; A61K 9/0019; A61K 9/4858; A61K 9/4866; A61K 36/07; A61K 45/06; A61P 35/00
See application file for complete search history.

(56) References Cited

U.S. PATENT DOCUMENTS

| 8,309,611 B2 * | 11/2012 | Liu | .......... C07C 403/02 |
| | | | 514/690 |
| 2012/0071426 A1 * | 3/2012 | Liu | .......... C07C 403/02 |
| | | | 514/25 |
| 2015/0025135 A1 * | 1/2015 | Liu | .......... A61K 9/0056 |
| | | | 514/473 |

OTHER PUBLICATIONS

Dan Faber Cancer Inst. Website, What is Refractory Cancer and How is it Treated, accessed Sep. 29, 2020, https://blog.dana-farber.org/insight/2018/01/refractory-disease-cancer/, by Ann LaCasce, MD, published Jan. 31, 2018. (Year: 2018).*
Nygaard et al. The Prognostic Value of KRAS mutated plasma DNA in advanced non-small cell lung cancer (Lung Cancer. Mar. 2013;79(3):312-7) (Year: 2013).*
Ho et al. Biomedicine & Pharmacotherapy vol. 68, Issue 8, Oct. 2014, pp. 1007-1014 (Year: 2014).*
EP application No. 17797009.2 Extended Search Report, dated Dec. 11, 2019.
SG application No. 11201810082V Search Report, dated Dec. 30, 2019.
SG application No. 11201810082V Second Written Opinion, dated Mar. 29, 2021.
Lee, Y.-C. et al., "A phase I multicenter study of antroquinonol in patients with metastatic non-small-cell lung cancer who have received at least two prior systemic treatment regimens, including one platinum-based chemotherapy regimen." *Mol Clin Oncol.*, Sep. 15, 2015, vol. 2015, No. 3, pp. 1375-1380.
History of Changes for Study: NCT01134016 Determine MTD and to Evaluate pk, Safety/Tolerability and Efficacy Profiles of Hocena® in NSCLC Subjects (Hocena). Nov. 4, 2014.
History of Changes for Study: NCT02047344 Efficacy, Safety and Pharmacokinetics Study of Antroquinonol to Treat NSCLC. Mar. 10, 2016.
Ho, C.-L. et al., "Antroquinonol blocks Ras and Rho signaling via the inhibition of protein isoprenyltransferase activity in cancer cells." *Biomedicine & Pharmacotherapy*, Sep. 26, 2014, vol. 68, No. 8, pp. 1007-1014.
Kumar, V. B. et al., "Antroquinonol inhibits NSCLC proliferation by altering PI3K/mTOR proteins and miRNA expression profiles." *Mutat Res.*, Dec. 24, 2010, vol. 707, No. 1-2, pp. 42-52.
Kempf, E. et al., "KRAS oncogene in lung cancer: focus on molecularly driven clinical trials." *European Respiratory Review*, Feb. 29, 2016, vol. 25, No. 139, pp. 71-76.
Villaume, M. T., et al., "Antroquinonol A: Scalable Synthesis and Preclinical Biology of a Phase 2 Drug Candidate", ACS Central Science, Dec. 23, 2015, vol. 2, No. 1, pp. 27-31.
Johnson L, et al., "K-*ras* is an essential gene in the mouse with partial functional overlap with N-*ras*," Genes Dev., 1997, vol. 11, pp. 2468-2481.

* cited by examiner

*Primary Examiner* — Jeffrey S Lundgren
*Assistant Examiner* — William Y Lee

(57) ABSTRACT

The present invention provides methods and compositions for treating advanced stage non-small cell lung cancer by cyclohexenone compounds.

9 Claims, No Drawings

METHODS AND COMPOSITIONS FOR TREATING ADVANCED STAGE NON-SMALL CELL LUNG CANCER

BACKGROUND OF THE INVENTION

Lung cancer is the most frequently diagnosed major cancer in the world and leading cause of cancer mortality worldwide. In the United States of America (USA), it was estimated that 219,440 new cases of lung cancer (116,090 men and 103,350 women) were diagnosed and 159,390 deaths were related to this malignancy in 2009. In Taiwan, 8,748 new cases of lung cancer were diagnosed in 2006, accounting for 11.94% of cancer diagnoses, and 7,479 patients died of this disease, contributing to 19.68% cancer deaths. The mortality was 44.42 and 20.65 per 100,000 men and women, respectively.

Lung cancers are categorized on the basis of important prognostic and therapeutic implications as either non-small cell lung cancer (NSCLC) or small cell lung cancer (SCLC). Non-small cell lung cancer contributed to about 80% of new cases diagnosed each year. NSCLC typically proliferates slower with lower doubling time than SCLC and can be characterized as three primary histologic types: adenocarcinoma, squamous cell, and large cell carcinoma. Adenocarcinoma has become the dominant histologic type of NSCLC and is the most common type in women and non-smokers. It typically arises in the periphery with glandular differentiation or mucin production, forms tubular or papillary structures, and metastasizes widely and early, compared to squamous carcinoma.

About 70% of NSCLC patients are diagnosed with advanced, poor-prognosis stage III or IV disease (approximately 50% for stage IV). The majority of these advanced tumors are considered inoperable due to disseminated (multiple sites) metastatic disease or metastatic sites that are not amendable to local therapy.

SUMMARY OF THE INVENTION

In one aspect provides herein for the treatment of advanced stage non-small cell lung cancer comprising administering to an individual a therapeutically effective amount of a cyclohexenone compound having the structure:

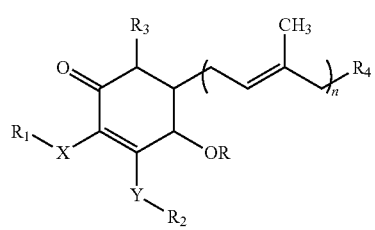

wherein each of X and Y is oxygen;
R is a hydrogen or $C(=O)C_1$-$C_8$alkyl;
each of $R_1$, $R_2$ and $R_3$ independently is a hydrogen, methyl or $(CH_2)_m$—$CH_3$;
$R_4$ is hydrogen; m=1-12,
n=1-12; or a pharmaceutically acceptable salt, metabolite, solvate or prodrug thereof.

In another aspect provides herein methods of treating an individual with non-small cell lung cancer stage IV comprising administering to a subject in need a therapeutically effective amount of a cyclohexenone compound having the structure:

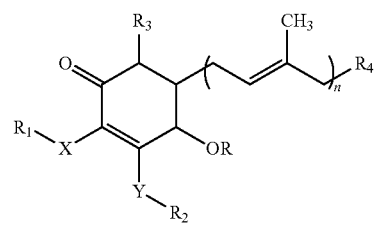

wherein each of X and Y is oxygen;
R is a hydrogen or $C(=O)C_1$-$C_8$alkyl;
each of $R_1$, $R_2$ and $R_3$ independently is a hydrogen, methyl or $(CH_2)_m$—$CH_3$;
$R_4$ is hydrogen; m=1-12,
n=1-12; or a pharmaceutically acceptable salt, metabolite, solvate or prodrug thereof.

In another aspect provides herein methods for improving or maintaining the quality of life of an individual diagnosed with non-small cell lung cancer stage IV comprising administering to said individual a therapeutically effective amount of a cyclohexenone compound having the structure:

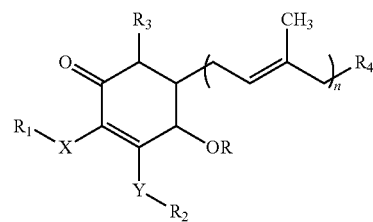

wherein each of X and Y is oxygen;
R is a hydrogen or $C(=O)C_1$-$C_8$alkyl;
each of $R_1$, $R_2$ and $R_3$ independently is a hydrogen, methyl or $(CH_2)_m$—$CH_3$;
$R_4$ is hydrogen; m=1-12,
n=1-12; or a pharmaceutically acceptable salt, metabolite, solvate or prodrug thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

About 70% of NSCLC patients are diagnosed with advanced, poor-prognosis stage III or IV disease (approximately 50% for stage IV). The majority of these advanced tumors are considered inoperable due to disseminated (multiple sites) metastatic disease or metastatic sites that are not amendable to local therapy. For these patients, platinum-based chemotherapy is the standard treatment recommended by American Society of Clinical Oncology and National Comprehensive Cancer Network (NCCN). Available treatment options, including systemic therapy using non-specific cytotoxic chemotherapy or targeted therapies, for advanced NSCLC have progressed significantly in the past two decades; however, survival for indicated patients remains modest. In addition, treatment for stage IV lung cancer remains a disappointment. Future directions toward new therapy are therefore necessary.

GTPase KRas also known as V-Ki-ras2 Kirsten rat sarcoma viral oncogene homolog and KRAS, is a protein that in human is encoded by the KRAS gene. The protein product of the normal KRAS gene performs an essential function in normal tissue signaling, and the mutation of a KRAS gene is an essential step in the development of many cancers. KRAS acts as a molecular on/off switch. Once it is turned on, it recruits and activates proteins necessary for the propagation of growth factor and other receptors' signal such as c-Raf and PI 3-kinase.

Whether a patient is positive or negative for a mutation in the epidermal growth factor receptor (EGFR) will predict how patients will respond to certain EGFR antagonists such as erlotinib (Tarceva) or gefitinib (Iressa). Patients who harbor an EGFR mutation have a 60% response rate to erlotinib. However, the mutation of KRAS and EGFR are generally mutually exclusive. Lung cancer patients who are positive for KRAS mutation (and the EGFR status would be wild type) have a low response rate to erlotinib or gefitinib estimated at 5% or less.

KRAS test is a genetic test designed to detect the presence of seven mutations in the KRAS gene in colorectal cancer cells. Identifying mutations in KRAS gene associated with NSCLC can help determine which patients are more likely to benefit from a targeted therapy.

It was surprisingly found that certain cyclohexenone compounds disclosed herein provide effective treatment outcome specifically for late stage NSCLC patients, especially for those patients who are positive in KRAS mutation.

The invention cyclohexenone compounds such as Compound 1, in some embodiments, are obtained from extracts of natural products or prepared synthetically or semi-synthetically, and provide reduced complications and/or side effects. Provided herein are methods for the treatment of advanced stage (e.g., Stage IV) non-small cell lung cancer by administering a cyclohexenone compound provided herein to an individual.

In some embodiments, there are provided methods for the treatment of advanced stage non-small cell lung cancer comprising administering to an individual a therapeutically effective amount of a cyclohexenone compound having the structure:

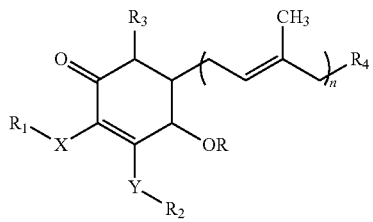

wherein each of X and Y is oxygen;
R is a hydrogen or $C(\!=\!O)C_1\text{-}C_8$alkyl;
each of $R_1$, $R_2$ and $R_3$ independently is a hydrogen, methyl or $(CH_2)_m\text{---}CH_3$ (i.e., an alkylene group);
$R_4$ is hydrogen; m=1-12,
n=1-12; or a pharmaceutically acceptable salt, metabolite, solvate or prodrug thereof. In certain embodiments, said advanced stage non-small cell lung cancer is non-small cell lung cancer stage IV.

In some embodiments, the methods reduce lung cancer tumor size or tumor volume. In some embodiments, the methods decrease lung cancer tumor growth rate.

In some embodiments provide methods of treating an individual with non-small cell lung cancer stage IV comprising administering to said individual in need a therapeutically effective amount of a cyclohexenone compound having the structure:

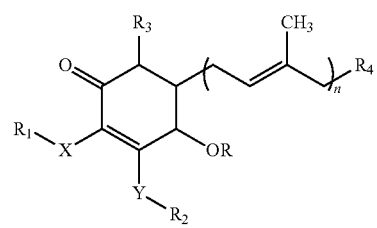

wherein each of X and Y is oxygen;
R is a hydrogen or $C(\!=\!O)C_1\text{-}C_8$alkyl;
each of $R_1$, $R_2$ and $R_3$ independently is a hydrogen, methyl or $(CH_2)_m\text{---}CH_3$;
$R_4$ is hydrogen; m=1-12,
n=1-12; or a pharmaceutically acceptable salt, metabolite, solvate or prodrug thereof.

In some embodiments, said method further comprising selecting an individual who has non-small cell lung cancer stage IV. The selection is based on the clinical setting known in the art.

In some embodiments provide methods for improving or maintaining the quality of life of an individual diagnosed with non-small cell lung cancer stage IV comprising administering to said individual a therapeutically effective amount of a cyclohexenone compound having the structure:

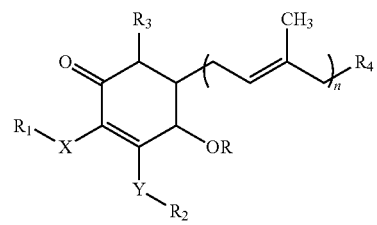

wherein each of X and Y is oxygen;
R is a hydrogen or $C(\!=\!O)C_1\text{-}C_8$alkyl;
each of $R_1$, $R_2$ and $R_3$ independently is a hydrogen, methyl or $(CH_2)_m\text{---}CH_3$;
$R_4$ is hydrogen; m=1-12,
n=1-12; or a pharmaceutically acceptable salt, metabolite, solvate or prodrug thereof.

In some embodiments, the cyclohexenone compound having the structure

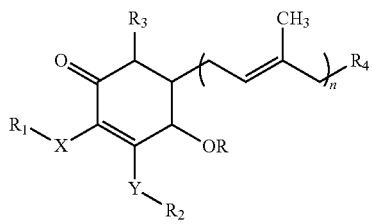

is prepared synthetically or semi-synthetically from any suitable starting materials. For example, Compound 1 (also known as Antroquinonol™ or "Antroq") or Compound 3, in some instances, is prepared from 4-hydroxy-2,3-dimethoxy-6-methylcyclohexa-2,5-dienone. The non-limited exemplary compounds are illustrated below.

1

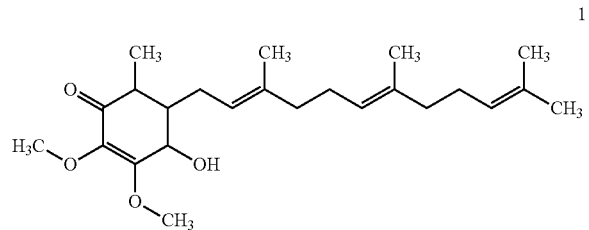

2

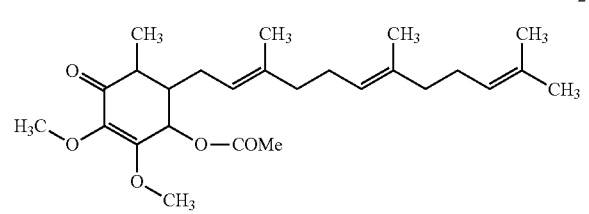

3

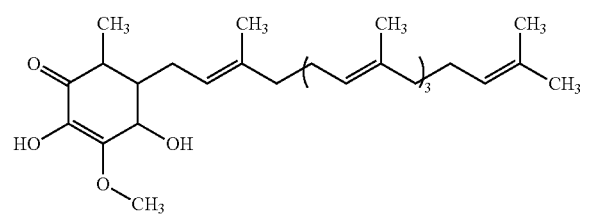

4

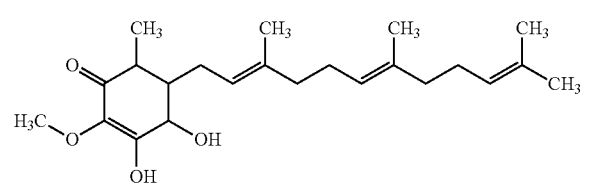

In other embodiments, the cyclohexenone compound having the structure

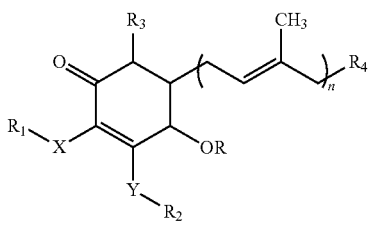

is isolated from the organic solvent extracts of a processed *Antrodia camphorate*. See e.g., U.S. Pat. No. 7,342,137. In some embodiments, the organic solvent is selected from alcohols (e.g., methanol, ethanol, propanol, or the like), esters (e.g., methyl acetate, ethyl acetate, or the like), alkanes (e.g., pentane, hexane, heptane, or the like), halogenated alkanes (e.g., chloromethane, chloroethane, chloroform, methylene chloride, and the like), and the like. For example, exemplary Compounds 1-7 are isolated from organic solvent extracts. In certain embodiments, the organic solvent is alcohol. In certain embodiments, the alcohol is ethanol. In some embodiments, the cyclohexenone compound is isolated from the aqueous extracts of *Antrodia camphorata*.

In some embodiments, R is a hydrogen, $C(=O)C_3H_8$, $C(=O)C_2H_5$, or $C(=O)CH_3$. In certain embodiments, $R_1$ is a hydrogen or methyl. In certain embodiments, $R_2$ is a hydrogen, methyl, ethyl, propyl, butyl, pentyl or hexyl. In some embodiments, $R_3$ is a hydrogen, methyl, ethyl, propyl, butyl, pentyl or hexyl. In certain embodiments, the compound is

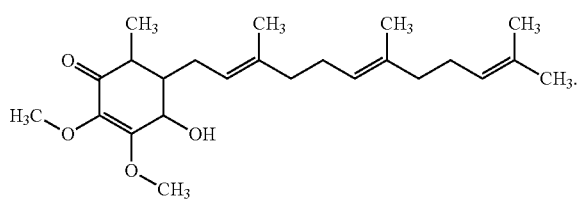 [SMILES: COC1=C(OC)C(O)C(C/C=C(\C)CC/C=C(\C)CCC=C(C)C)C(C)C1=O]

In some embodiments, said individual is KRAS positive. In some embodiments, said individual is a patient who has failed at least two lines of anti-cancer therapy.

In some embodiments, said cyclohexenone compound, or a pharmaceutically acceptable salt, metabolite, solvate or prodrug thereof, is administered parenterally, intravenously, orally, or by injection. In some embodiments, the dose of said cyclohexenone compound is about 600 mg per day. In certain embodiments, said individual is cancer free after 12 weeks of administration of said compound in accordance with the methods provided herein.

Dosages

One of skill in the art understands that the dosage may depend on several factors, including, but not limited to, the individual's weight, tumor size, or tumor progression. Exemplary compound such as Compound 1 in some instances is administered as a single agent at a dose of 600 mg per day (200 mg t.i.d. administered at 8-hour intervals). There were no significant differences in $AUC_{0-24}$ in the 100-300 mg dose range. Thus, in some instances, the dosage may be reduced to 100-300 mg per day. In some embodiments, in order to maintain a high drug concentration and enhance the efficacy of Compound 1, the regiment of 200 mg t.i.d. (every eight hours) has been chosen preferably.

An individual may be given a dose of about 50 mg, about 100 mg, about 200 mg, about 300 mg, about 400 mg, about 500 mg, about 600 mg, about 700 mg, about 800 mg, or about 800 mg or more of Compound 1, in either single or cumulative applications.

In selecting an individual with NSCLC for treatment with the invention compound, it may be beneficial to determine if the patient is KRAS positive or negative. Surprisingly, the invention compound such as Compound 1 exhibit good treatment results with those having NSCLC stage IV with and without KRAS mutations. In some embodiments, those patients with KRAS positive benefit with the method of treatments disclosed herein.

Individuals with Different NSCLC Stages

When individuals with NSCLC are to be treated with a cyclohexenone compound of the invention, individuals diagnosed as having advanced stage such as stage IV with or without malignant pleural effusion specifically may be treated.

Generally, when the invention compounds are used in individuals with NSCLC, the stage of NSCLC in the individual may be determined before, after, or during treatment. An outline of lung cancer staging is set forth below:

Normally in lung cancer, an increasing "stage" number correlates with a worse prognosis. To diagnose an individual at a cancer stage, the size and the location of the primary tumor ("T" value), as well as the degree of nodal involvement and increasing probability of metastases ('N' value), are taken into consideration. Also noted when diagnosing individuals is the absence ("M0") or presence ("M1") of metastases.

1. T Category

The T category is made up of subcategories, T1-T4, whereby an increasing number from 1 to 4 represents increasing size and local invasion by the primary tumor. T1 and T2 are differentiated primarily on size, for example T1 is less than 3 cm, while T2 is larger than 3 cm. T3 tumors typically involve the chest wall, and include, but are not limited to the superior pulmonary sulcus, diaphragm, mediastinal pleura, pericardium or proximal main stem bronchus, but may be resectable. T4 tumors are not surgically resectable because they may have invaded the mediastinum and may involve the heart, great vessels, trachea, carina or esophagus, or in the case of a malignant pleural effusion, the pleura.

2. N Category

Nodal stages are divided into N1, N2, and N3. N1 nodes typically involve peribronchial or ipsilateral hilar nodes. These nodes are intrapleural in position. N2 nodes typically involve ipsilateral mediastinal or subcarinal nodes. N3 nodes typically involve contralateral hilar, or mediastinal, any scalene nodes, or supraclavicular nodes.

3. NSCLC Stages

The "stages" of NSCLC, therefore, represent distinct classifications of NSCLC that are based on the various permutations of T, N, and M values. The recognized stages of NSCLC are as follows:

Occult Carcinoma: In this category, patients are classified as TX N0 M0, meaning that they have had malignant cells detected in their bronchopulmonary secretions, but there is no tumor evident by bronchoscopic or radiographic methods.

Stage IA and Stage IB: Stage IA is classified as T1 N0 M0 based upon a significantly higher 5-year survival outcome than patients with stage IB disease (T2 N0 M0). Surgery is the preferred treatment for these patients. For example, in 1997, the 5-year survival rate for patients surgically staged as stage IA was 67% and for stage IB was 57%.

Stage IIA and Stage IIB: Stage IIA disease is defined as T1 N1 M0 and has a 55% survival rate at 5 years based on surgical staging. Stage IIB disease is composed of T2 N1 M0 and T3 N0 M0. The designation of T3 N0 M0 represents extrapulmonary extension of the tumor without lymph node involvement. The classification T3 N0 M0 is grouped with T2 N1 M0 because their respective 5-year survival rates for surgically staged disease, 38% versus 39%, are not significantly different. Surgery is also the primary treatment for these individuals.

Stage IIIA: Stage IIIA patients are considered to be resectable, while Stage IIIB patients are not. Stage IIIA patients are defined by lesions with extrapulmonary extension (T3) and limited lymph node involvement (N1 or N2). The nodal involvement may extend to the ipsilateral mediastinal, and/or subcarinal lymph nodes. These patients are classified as either T3 N1 M0, or T1-3 N2 M0. For example, as of 1997, the 5-year survival rate for stage IIIA disease was 23%.

Stage IIIB: Stage IIIB classification refers to patients who have extrapulmonary involvement including, but not limited to contralateral mediastinal or hilar lymph nodes; ipsilateral or contralateral supraclavicular or scalene nodes; extensive mediastinal nodes without distant metastases; or cytology positive malignant pleural effusion. These patients can be classified as either T1-3 N3 M0 or T4 N0-3 M0. For example, in 1997, the 5-year survival rate for clinically staged disease was 5% with multimodal therapy.

Stage IV: Stage IV is defined by any metastatic involvement. These patients are classified as M1 with any T and any N. For example, as of 1997, more than a quarter of patients with NSCLC had clinical stage IV.

An ordinary skilled person the in the art would readily apply other similar, and suitable methods in categorizing the stages of NSCLC and for patient selections.

Certain Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl group may be a saturated alkyl group (which means that it does not contain any carbon-carbon double bonds or carbon-carbon triple bonds) or the alkyl group may be an unsaturated alkyl group (which means that it contains at least one carbon-carbon double bonds or carbon-carbon triple bond). The alkyl moiety, whether saturated or unsaturated, may be branched, or straight chain.

The "alkyl" group may have 1 to 12 carbon atoms (whenever it appears herein, a numerical range such as "1 to 12 refers to each integer in the given range; e.g., "1 to 12 carbon atoms" means that the alkyl group may consist of 1 carbon atom, 2 carbon atoms, 3 carbon atoms, etc., up to and including 12 carbon atoms, although the present definition also covers the occurrence of the term "alkyl" where no numerical range is designated). The alkyl group of the compounds described herein may be designated as "$C_1$-$C_8$ alkyl" or similar designations. By way of example only, "$C_1$-$C_8$ alkyl" indicates that there are one, two, three, four, five, six, seven or eight carbon atoms in the alkyl chain. In one aspect the alkyl is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, allyl, but-2-enyl, but-3-enyl, cyclopropylmethyl, cyclobutylmethyl, cyclopentylmethyl, cyclohexylmethyl, and the like. In one aspect, an alkyl is a $C_1$-$C_8$ alkyl.

The term "alkylene" refers to a divalent alkyl radical. Any of the above mentioned monovalent alkyl groups may be an alkylene by abstraction of a second hydrogen atom from the alkyl. In one aspect, an alkylene is a $C_1$-$C_{12}$alkylene (e.g., —$(CH_2)_m$—$CH_3$). In another aspect, an alkylene is a $C_1$-$C_8$alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

The term "alkenyl" as used herein, means a straight, branched chain, or cyclic (in which case, it would also be known as a "cycloalkenyl") hydrocarbon containing from 2-10 carbons and containing at least one carbon-carbon double bond formed by the removal of two hydrogens. In some embodiments, depending on the structure, an alkenyl group is a monoradical or a diradical (i.e., an alkenylene group). In some embodiments, alkenyl groups are optionally substituted. Illustrative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-cecenyl.

The term "alkynyl" as used herein, means a straight, branched chain, or cyclic (in which case, it would also be known as a "cycloalkenyl") hydrocarbon containing from 2-10 carbons and containing at least one carbon-carbon triple bond formed by the removal of four hydrogens. In some embodiments, depending on the structure, an alkynyl group is a monoradical or a diradical (i.e., an alkynylene group). In some embodiments, alkynyl groups are optionally substituted. Illustrative examples of alkynyl include, but are not limited to, ethynyl, propynyl, butynyl, pentynyl, hexynyl, heptynyl, and the like.

Certain Pharmaceutical and Medical Terminology

The term "acceptable" with respect to a formulation, composition or ingredient, as used herein, means having no persistent detrimental effect on the general health of the subject being treated.

*Antrodia* is a genus of fungi in the family Meripilaceae. *Antrodia* species have fruiting bodies that typically lie flat or spread out on the growing surface, with the hymenium exposed to the outside; the edges may be turned so as to form narrow brackets. Most species are found in temperate and boreal forests, and cause brown rot. Some of the species in this genus are have medicinal properties, and have been used in Taiwan as a Traditional medicine.

The term "carrier," as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound (i.e., a cyclohexenone compound described herein) and a co-agent, are both administered to a patient simultaneously in the form of a single entity or dosage. The term "non-fixed combination" means that the active ingredients, e.g. a compound (i.e., a cyclohexenone compound described herein) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound (i.e., a cyclohexenone compound described herein) with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

In some embodiments, the cyclohexenone compound, or a pharmaceutically acceptable salt, metabolite, solvate or prodrug thereof, is administered parenterally or intravenously. In other embodiments, the cyclohexenone compound, or a pharmaceutically acceptable salt, metabolite, solvate or prodrug thereof, is administered by injection. In some embodiments, the cyclohexenone compound, or a pharmaceutically acceptable salt, metabolite, solvate or prodrug thereof, is administered orally.

Pharmaceutical Composition/Formulation

In some embodiments provide compounds having the structure:

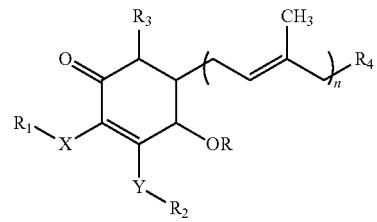

wherein each of X and Y is oxygen;
R is a hydrogen or $C(=O)C_1-C_8$alkyl;
each of $R_1$, $R_2$ and $R_3$ independently is a hydrogen, methyl or $(CH_2)_m-CH_3$;
$R_4$ is hydrogen; m=1-12,
n=1-12; or a pharmaceutically acceptable salt, metabolite, solvate or prodrug thereof.

In some embodiments, R is a hydrogen, $C(=O)C_3H_8$, $C(=O)C_2H_5$, or $C(=O)CH_3$. In some embodiments, each of $R_1$, $R_2$ and $R_3$ independently is a hydrogen, methyl, ethyl, propyl, butyl, pentyl hexyl, heptyl, or octyl. In certain embodiments, $R_1$ is a hydrogen or methyl. In certain embodiments, $R_2$ is a hydrogen, methyl, ethyl, propyl, butyl, pentyl or hexyl. In certain embodiments, $R_3$ is a hydrogen, methyl, ethyl, propyl, butyl, pentyl or hexyl.

In certain embodiments, the compound is selected from group consisting of

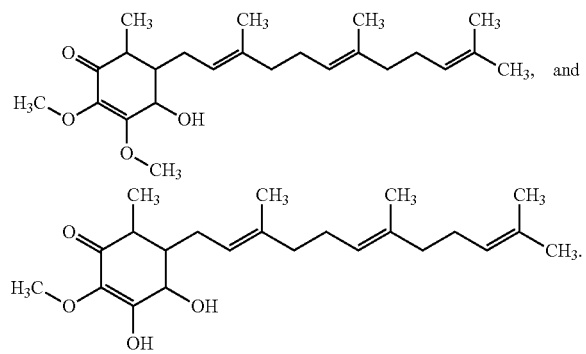

In some embodiments provide pharmaceutical compositions comprising a therapeutically effective amount of a cyclohexenone compound having the structure:

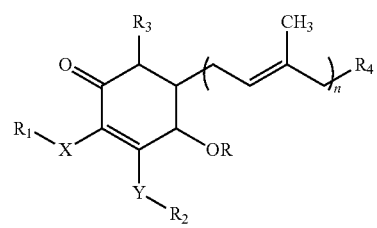

wherein each of X and Y is oxygen;

R is a hydrogen or C(=O)C$_1$-C$_8$alkyl;

each of R$_1$, R$_2$ and R$_3$ independently is a hydrogen, methyl or (CH$_2$)$_m$—CH$_3$;

R$_4$ is hydrogen; m=1-12, n=1-12; or a pharmaceutically acceptable salt, metabolite, solvate or prodrug thereof.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

Provided herein are pharmaceutical compositions comprising a compound (i.e., a cyclohexenone compound described herein) and a pharmaceutically acceptable diluent(s), excipient(s), or carrier(s). In certain embodiments, the compounds described are administered as pharmaceutical compositions in which a compound (i.e., a cyclohexenone compound described herein) is mixed with other active ingredients, as in combination therapy. Encompassed herein are all combinations of actives set forth in the combination therapies section below and throughout this disclosure. In specific embodiments, the pharmaceutical compositions include one or more compounds (i.e., a cyclohexenone compound described herein).

A pharmaceutical composition, as used herein, refers to a mixture of a compound (i.e., a cyclohexenone compound described herein) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds (i.e., a cyclohexenone compound described herein) are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, a compound (i.e., a cyclohexenone compound described herein) is formulated in an aqueous solution. In specific embodiments, the aqueous solution is selected from, by way of example only, a physiologically compatible buffer, such as Hank's solution, Ringer's solution, or physiological saline buffer. In other embodiments, a compound (i.e., a cyclohexenone compound described herein) is formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or nonaqueous solutions. In specific embodiments, such solutions include physiologically compatible buffers and/or excipients.

In another embodiment, compounds described herein are formulated for oral administration. Compounds described herein, including a compound (i.e., a cyclohexenone compound described herein), are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipients with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions of a compound (i.e., a cyclohexenone compound described herein) are formulated in a form suitable for parenteral injection as a sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In one aspect, compounds (i.e., cyclohexenone compounds described herein) are prepared as solutions for parenteral injection as described herein or known in the art and administered with an automatic injector. Automatic injectors, such as those disclosed in U.S. Pat. Nos. 4,031,893, 5,358,489; 5,540,664; 5,665,071, 5,695,472 and WO/2005/087297 (each of which are incorporated herein by reference for such disclosure) are known. In general, all automatic injectors contain a volume of solution that includes a compound (i.e., a cyclohexenone compound described herein) to be injected. In general, automatic injectors include a reservoir for holding the solution, which is in fluid communication with a needle for delivering the drug, as well as a mechanism for automatically deploying the needle, inserting the needle into the patient and delivering the dose into the patient. Exemplary injectors provide about 0.3 mL, 0.6 mL, 1.0 mL or other suitable volume of solution at about a concentration of 0.5 mg to 50 mg of a compound (i.e., a cyclohexenone compound described herein) per 1 mL of solution. Each injector is capable of delivering only one dose of the compound.

In still other embodiments, the compounds (i.e., cyclohexenone compounds described herein) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds (i.e., cyclohexenone compounds described herein) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of a compound (i.e., a cyclohexenone compound described herein) is accomplished by means of iontophoretic patches and the like. In certain embodiments, transdermal patches provide controlled delivery of a compound (i.e., a cyclohexenone compound described herein). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients which are conventional in the art. In one embodiment, the transdermal formulations described herein include at least three components: (1) a formulation of a compound (i.e., a cyclohexenone compound described herein); (2) a penetration enhancer; and (3) an aqueous adjuvant. In addition, transdermal formulations can include additional components such as, but not limited to, gelling agents, creams and ointment bases, and the like. In some embodiments, the transdermal formulations further include a woven or nonwoven backing material to enhance absorption and prevent the removal of the transdermal formulation from the skin. In other embodiments, the transdermal formulations described herein maintain a saturated or supersaturated state to promote diffusion into the skin.

In other embodiments, the compounds (i.e., cyclohexenone compounds described herein) are formulated for administration by inhalation. Various forms suitable for administration by inhalation include, but are not limited to, aerosols, mists or powders. Pharmaceutical compositions of a compound (i.e., a cyclohexenone compound described herein) are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatins for use in an inhaler or insufflator are formulated containing a powder mix of the compound and a suitable powder base such as lactose or starch.

Intranasal formulations are known in the art and are described in, for example, U.S. Pat. Nos. 4,476,116, 5,116,817 and 6,391,452, each of which is specifically incorporated herein by reference. Formulations, which include a compound (i.e., a cyclohexenone compound described herein), which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are found in sources such as REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the compounds described herein, may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

In still other embodiments, the compounds (i.e., cyclohexenone compounds described herein) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients is optionally used as suitable and as understood in the art. Pharmaceutical compositions comprising a compound (i.e., a cyclohexenone compound described herein) may be manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound (i.e., cyclohexenone compounds described herein) described herein as an active ingredient. The active ingredient is in free-acid or free-base form, or in a pharmaceutically acceptable salt form. In addition, the methods and pharmaceutical compositions described herein include the use crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least compound (i.e., cyclohexenone compounds described herein) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, pharmaceutical aqueous suspensions include one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein include a mucoadhesive polymer, selected from, for example, carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally include solubilizing agents to aid in the solubility of a compound (i.e., cyclohexenone compounds described herein). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other pharmaceutical compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other pharmaceutical compositions may include one or more antioxidants to enhance chemical stability where required. Suitable antioxidants include, by way of example only, ascorbic acid and sodium metabisulfite.

In certain embodiments, pharmaceutical aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few hours up to over 24 hours. Depending on the chemical nature and the biological stability of the therapeutic reagent, additional strategies for protein stabilization may be employed.

In certain embodiments, the formulations described herein include one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Combination Treatments

In general, the compositions described herein and, in embodiments where combinational therapy is employed, other agents do not have to be administered in the same pharmaceutical composition, and in some embodiments, because of different physical and chemical characteristics, are administered by different routes. In some embodiments, the initial administration is made according to established protocols, and then, based upon the observed effects, the dosage, modes of administration and times of administration is modified by the skilled clinician.

In some embodiments, therapeutically-effective dosages vary when the drugs are used in treatment combinations. Combination treatment further includes periodic treatments that start and stop at various times to assist with the clinical management of the patient. For combination therapies described herein, dosages of the co-administered compounds vary depending on the type of co-drug employed, on the specific drug employed, on the disease, disorder, or condition being treated and so forth.

It is understood that in some embodiments, the dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in other embodiments, the dosage regimen actually employed varies widely and therefore deviates from the dosage regimens set forth herein.

Combinations of compounds (i.e., the cyclohexenone compound described herein) with other anti-cancer agents are intended to be covered. In some embodiments, examples of anti-cancer agents include, but are not limited to, the following: cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristin, vinblastin and methotrexate, other topoisomerase inhibitors (e.g., irinotecan, topotecan, camptothecin, etc.) or any derivative related agent of the foregoing.

The combinations of the cyclohexenone compounds and other anti-cancer agents described herein encompass additional therapies and treatment regimens with other agents in some embodiments. Such additional therapies and treatment regimens can include another anti-cancer therapy in some embodiments. Alternatively, in other embodiments, additional therapies and treatment regimens include other agents used to treat adjunct conditions associated with the cancer or a side effect from such agent in the combination therapy. In further embodiments, adjuvants or enhancers are administered with a combination therapy described herein.

Additional anti-cancer therapies include chemotherapy, radiotherapy, immunotherapy, gene therapy, surgery or other therapies that are capable of negatively affecting cancer in a patient, such as for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

EXAMPLES

Example 1. Preparation of the Exemplary Cyclohexenone Compounds

One hundred grams of mycelia, fruiting bodies or mixture of both from *Antrodia camphorata* were placed into a flask. A proper amount of water and alcohol (70-100% alcohol solution) was added into the flask and were stirred at 20-25° C. for at least 1 hour. The solution was filtered through a filter and 0.45 μm membrane and the filtrate was collected as the extract.

The filtrate of *Antrodia camphorata* was subjected to High Performance Liquid chromatography (HPLC) analysis. The separation was performed on a RP18 column, the mobile phase consisted of methanol (A) and 0.3% acetic acid (B), with the gradient conditions of 0-10 min in 95%-20% B, 10-20 min in 20%-10% B, 20-35 min in 10%-10% B, 35-40 min in 10%-95% B, at the flow rate of 1 ml/min. The column effluent was monitored with a UV-visible detector.

The fractions collected at 21.2 to 21.4 min were collected and concentrated to yield compound 5, a product of pale yellow liquid. Compound 5 was analyzed to be 4-hydroxy-5-(11-hydroxy-3,7,11-trimethyldodeca-2,6-dienyl)-2,3-dimethoxy-6-methylcyclohex-2-enone with molecular weight of 408 (Molecular formula: $C_{24}H_{40}O_5$).

The fractions collected at 23.7 to 24.0 min were collected and concentrated to yield compound 7, a product of pale yellow liquid. Compound 7 was analyzed to be 4-hydroxy-2,3-dimethoxy-5-(11-methoxy-3,7,11-trimethyldodeca-2,6-dienyl)-6-methylcyclohex-2-enone with molecular weight of 422 ($C_{25}H_{42}O_5$).

The fractions collected at 25 to 30 min were collected and concentrated to yield 4-hydroxy-2,3-dimethoxy-6-methyl-5-(3,7,11-trimethyldodeca-2,6,10-trienyl)cyclohex-2-enone (compound 1), a product of pale yellow brown liquid. The analysis of Compound 1 showed the molecular formula of $C_{24}H_{38}O_4$, molecular weight of 390 with melting point of 48 to 52° C. NMR spectra showed that $^1$H NMR (CDCl$_3$) δ (ppm)=1.51, 1.67, 1.71, 1.75, 1.94, 2.03, 2.07, 2.22, 2.25, 3.68, 4.05, 5.07, and 5.14; $^{13}$C-NMR (CDCl$_3$) δ (ppm)= 12.31, 16.1, 16.12, 17.67, 25.67, 26.44, 26.74, 27.00, 39.71, 39.81, 40.27, 43.34, 59.22, 60.59, 120.97, 123.84, 124.30, 131.32, 135.35, 135.92, 138.05, 160.45, and 197.12.

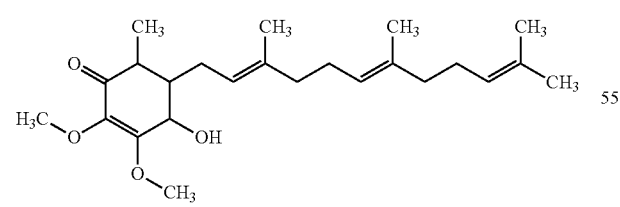

Compound 1: 4-hydroxy-2,3-dimethoxy-6-methyl-5-(3,7,11-trimethyldodeca-2,6,10-trienyl)cyclohex-2-enone Compound 6, a metabolite of Compound 1, was obtained from urine samples of rats fed with Compound 1 in the animal study. Compound 6 was determined to be 4-hydroxy-2,3-dimethoxy-6-methyl-5-(3-methyl-2-hexenoic acid)cyclohex-2-enone with molecular weight of 312 ($C_{16}H_{24}O_6$). Compound 4 which was determined as 3,4-dihydroxy-2-methoxy-6-methyl-5-(3,7,11-trimethyldodeca-2,6,10-trienyl)cyclohex-2-enone (molecular weight of 376, $C_{23}H_{36}O_4$), was obtained when Compound 1 was under the condition of above 40° C. for 6 hours.

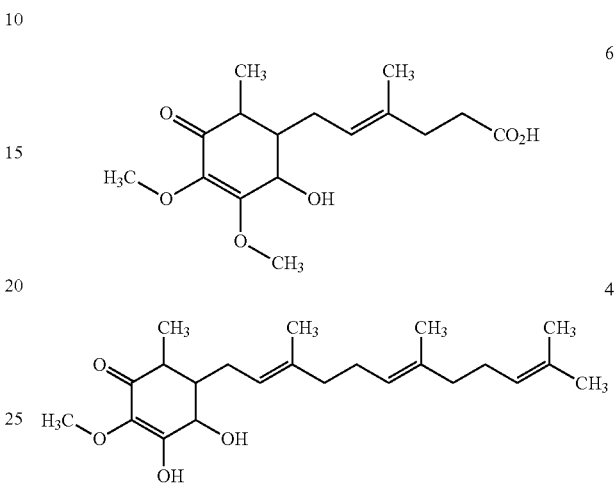

Alternatively, the exemplary compounds may be prepared synthetically from suitable starting material such as 4-hydroxy-2,3-dimethoxy-6-methylcyclohexa-2,5-dienone, or the like. See for example, U.S. Pat. No. 9,365,481.

Similarly, other cyclohexenone compounds having the structure

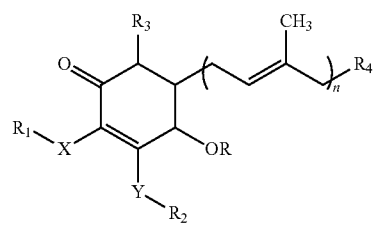

are isolated from *Antrodia camphorata* or prepared synthetically or semi-synthetically from the suitable starting materials. An ordinary skilled in the art would readily utilize appropriate conditions for such synthesis.

Example 2. Preclinical Study of Exemplary Compound 1

Exemplary Compound 1 caused cell death with an IC50 of 2.22 to 6.42 μM for different cancer cell lines. Compound 1 significantly enhanced the ratio of unprocessed to processed Ras in lung cancer cells in a dose-dependent manner (P<0.01) and this enhancement was competed by farnesyl pyrophosphate. Compound 1 inhibited isoprenyltransferase activity and molecular docking analysis predicted that the isoprene unit and the 4'-hydroxy group of Compound 1 may play important roles in the interaction between Compound 1 and isoprenyltransferase. In addition, Compound 1 increased the expression level of beclin-1 (three-fold), LC3-II/I (P<0.01) and PC3 puncta formation in lung cancer cells.

Compound 1 may therefore inhibit Ras activation through inhibition of isoprenyltransferase, leading to autophagic cell death.

Previous studies revealed that the invention cyclohexenone compounds such as Compound 1 triggers anti-tumor activity through several signaling molecules, including AMPK, PI3K, and mTOR. Recent research suggests that Compound 1 indirectly inhibits Ras processing through inhibition of isoprenyltransferase activity. The Ras-PI3K-Akt-mTOR pathway, which is associated with proliferation, motility, metabolism, and differentiation, is inhibited in response to Compound 1. Thus, exemplary Compound 1 may promote its anti-cancer effects by regulating cross talk in a complex signaling network that results in apoptosis and autophagy.

An in vivo study in non-obese diabetes/severe combined immunodeficiency mice with A549 subcutaneous xenografts consistently showed tumor growth suppression results after 2 weeks of oral 30 and 60 mg/kg Compound 1 treatment. Safety pharmacology studies including central nervous system effect in Sprague-Dawley rat, binding activity with hERG ion channel in in vitro setting, cardiovascular effect in beagle dogs and respiratory system effect study in Sprague-Dawley rat were all completed and the results showed no particular safety concerns of Compound 1. Pharmacokinetic (PK) studies including absolute bioavailability determination, organ distributions, metabolism related to cytochrome P450 (CYP), main metabolites in rat urine and cross-species metabolite comparisons were all completed, with results indicating fast absorption, substantial organ distribution especially in the lung, heart, and kidney, and CYP involved metabolism profiles of Compound 1.

Previously two 7-day toxicity studies were performed in both Sprague-Dawley rats and beagle dogs and the maximum tolerated doses (MTD) determined were between 100 mg/kg/day for rats and 100 mg/kg/day for dogs. Two 28-days toxicity studies were conducted to determine no observed adverse effect level (NOAEL) for Sprague-Dawley rats and beagle dogs. The rat NOAEL was 30 mg/kg/day and the high dose of 100 mg/kg/day was not severely toxic.

A NOAEL in the dog was not identified (i.e., loose feces, liquid feces, and vomiting were observed at all doses); the 30 mg/kg/day dose level was tolerated and is the highest non-severely toxic dose (HNSTD).

Toxicokinetic evaluations were performed on a 7-day dog study (100, 250, 500 mg/kg/day single dose, 500 mg/kg/day 3 days dose) and the two 28-day studies mentioned above (Rat: 10, 30, 100 mg/kg/day single and 28 days dose; Dog: 10, 30, 100 mg/kg/day single and 28 days dose). Fast absorption of Compound 1 was repeatedly seen in rats and dogs with peak time ($T_{max}$) ranging from 0.25 to 6 hours. A trend of dose proportionality in the rat and dog was more or less shown after 1 day of treatment. After 28 days of treatment, rat and dog studies showed inconsistent phenomena in dose proportionality view, one was greater and the other was less than linear in the dose-exposure relationship.

No genotoxicity and no reproductive toxicity (up to 80 mg/kg/day) of the exemplary Compound 1 was observed via Ames test, mammalian cell gene mutation test, micronucleus test, erythrocyte micronucleus test and in vivo study in Sprague-Dawley rats.

Example 3. Phase 1 Clinical Study of Compound 1

A first-in-human phase 1 study was performed to determine the MTD and to evaluate PK, safety/tolerability and efficacy profiles of exemplary Compound 1 in NSCLC patients who are refractory to conventional treatment modalities. This open-label, non-randomized, dose-escalation study, which completed in February 2013, enrolled a total of 13 patients; seven males and six females, all of whom were Asian. A total of five patients were enrolled an accelerated titration phase (one patient each in the 50, 100, 200, 300, and 450 mg dose groups) and eight patients were enrolled in a standard titration phase (three patients in the 450 mg dose group and five patients in the 600 mg dose group).

No Dose Limiting Toxicities (DLTs) were reported in any patient for any of the doses (50, 100, 200, 300, 450, and 600 mg) in the Intent-to-Treat Population in the accelerated titration phase or standard titration phase.

Pharmacokinetic results indicated that the rate and extent of absorption of Compound 1 increased in a dose proportional manner over the dosing range of 50 to 600 mg after multiple administrations of Compound 1. However, the rate and extent of Compound 1 absorption increased in a non-dose proportional and a dose proportional manner, respectively, over the dosing range of 50 to 600 mg under single dose conditions. No clear trend was observed when comparing the PK parameters under single dose conditions to those under multiple dose conditions.

Efficacy results indicated that the tumor overall response at the end of treatment showed stable disease progress for three patients (out of the all enrolled patients) included in the Per-Protocol population: one patient in the 200 mg dose group and two patients in the 600 mg dose group (100%).

Safety results indicated that exemplary Compound 1 at 50, 100, 200, 300, 450, and 600 mg dose levels, given daily for 4 weeks, was generally safe and well tolerated. Compound 1 at 50, 100, 200, 300, 450, and 600 mg dose levels exhibited a low toxicity profile. Overall, four patients reported four serious adverse events (SAEs) with two patients each in the 450 and 600 mg dose groups. Of these, one patient from each dose group died due to progressive disease and discontinued from the study (one patient in the 600 mg dose group discontinued due to the adverse event [AE] of pleural effusion). None of the deaths, SAEs, and AEs leading to discontinuations was related to the study drug. No Grade 4 treatment-emergent adverse events (TEAEs) were reported as determined by the National Cancer Institute-Common Terminology Criteria for Adverse Events (NCI-CTCAE), Version 4.03.

Treatment-emergent AEs of toxicity Grade 3 were reported in two patients (one patient in the 200 mg dose group experienced vertigo and one patient in the 450 mg dose group experienced decreased appetite and encephalitis); all events were unrelated to the study drug.

All 13 (100%) patients treated reported TEAEs that were considered treatment-related. The most commonly occurring TEAEs, reported in >two patients, overall, were in the system organ classes of gastrointestinal disorders (12 patients, 92.3% [seven patients in Grade 1, 53.8%, and five patients in Grade 2, 38.5%]), and by preferred term were diarrhea (10 patients, 76.9% [nine patients in Grade 1, 69.2%, and one patient in Grade 2, 7.7%]), vomiting (nine patients, 69.2% [six patients in Grade 1, 46.2%, and three patients in Grade 2, 23.1%]), and nausea (seven patients, 53.8% [six patients in Grade 1, 46.2%, and one patient in Grade 2, 7.7%]).

No patient had any laboratory abnormality recorded as a TEAE except for one case of hematuria of Grade 1 in the 450 mg dose group. Per the sonogram report of the kidney, stones sized 0.47 cm and 0.50 cm in the left kidney without hydronephrosis were noted. The event was considered to be unrelated to the study drug. There were slight increases or decreases in the hematology and biochemistry parameters but none were considered abnormal results.

For urinalysis, at Cycle 1 baseline, four patients had abnormal urinalysis results: one patient each in the 200 and 600 mg dose groups and two patients in the 450 mg dose group. At follow-up, five patients had abnormal urine values: two patients in the 450 mg group that had abnormal values at baseline and three new patients at lower dose levels (one patient each in the 50, 100, and 300 mg dose groups).

None of the patients were reported to have clinically significant changes in any of the vital sign, electrocardiogram (ECG), and physical examination parameters at the Follow-Up Visit.

The Eastern Cooperative Oncology Group (ECOG) score was 1 for all patients at all time points, except for two patients in the 450 mg group who had an ECOG score of 4 (completely disabled, cannot carry on any self-care) at the Follow-Up Visit and a score of 2 (ambulatory and capable of all self-care but unable to carry out any work activities) at the Cycle 3, Day 28 visit. The results indicate the possible different treatment effects among patients enrolled in the study, which triggered the study to find out if the exemplary compound 1 is especially effective for patients with late stage NSCLC and/or can provide other therapeutically benefit against NSCLC unexpectedly.

Example 4: Clinical Study in Patients with Stage IV (Including Pleural Effusion) Non-Squamous Non-Small Cell Lung Cancer (NSCLC) with Compound 1

In the phase 1 study in NSCLC patients refractory to conventional treatment modalities, Compound 1 at 50, 100, 200, 300, 450, and 600 mg dose levels, given daily for 4 weeks, was generally safe and well tolerated as no particular safety concerns or DLTs were identified in the study. In addition, efficacy results indicated that the tumor overall response at the end of treatment showed stable disease for all three patients with satisfied results included in the per-protocol population: one patient in the 200 mg dose group and two patients in the 600 mg dose group (100%). Therefore its progression to further clinical development is warranted in a larger number of patients with NSCLC.

Study Objectives

Primary Objective:

To evaluate the activity of Compound 1 in unselected, KRAS-positive, and KRAS-negative patients with stage IV (including pleural effusion) non-squamous NSCLC who have failed two lines of anti-cancer therapy.

Secondary Objective:

To assess the safety and tolerability and PK of Compound 1 in patients with stage IV (including pleural effusion) non-squamous NSCLC who have failed two lines of anti-cancer therapy.

Exploratory Objective:

To explore potential relationships between Compound 1 exposure and safety and efficacy endpoints.

Overall Study Design and Plan

Description:

This is a single-arm, open-label, Phase II study in KRAS-positive and KRAS-negative patients with stage IV (including pleural effusion) non-squamous NSCLC who have failed two lines of anti-cancer therapy. This is defined as patients with radiologically confirmed disease progression following greater than or equal to two, but less than or equal to four, prior lines of systemic anti-cancer therapy. A maximum of 60 evaluable patients with NSCLC will receive Compound 1, of which 30 patients will be KRAS-positive and 30 patients KRAS-negative. An evaluable patient will have received at least one dose of Compound 1 and have a valid baseline tumor assessment. Enrollment will continue until the target number of evaluable patients has been enrolled.

Written informed consent must be obtained from all patients before initiating Screening. The Screening period will be up to 42 days in duration (Days −42 to −1). Following completion of all Screening assessments and confirmation of eligibility criteria, patients will receive Compound 1 200 mg three-times-a-day (t.i.d. at 8-hour intervals) on Day 0 for 12 weeks (one treatment cycle) or until documented evidence of disease progression, unacceptable toxicity, non-compliance or withdrawal of consent by the patient, or the investigator decides to discontinue treatment, whichever comes first. Study drug should be taken at 8-hour intervals. The time of study drug administration should be recorded in the patient diary.

After the first 12-week treatment cycle, patients who are progression-free will be eligible to receive further (12-week) treatment cycles with Compound 1 (Extension Phase), until documented evidence of disease progression, unacceptable toxicity, non-compliance or withdrawal of consent by the patient, or the investigator decides to discontinue treatment, whichever comes first. Investigators should wait at least 7 days after the last administration of study drug before initiating alternative treatment.

Patients will attend study visits on Days 0, 14, 28, 42, 56 and 84 during the first 12-week treatment cycle, every 4 weeks during the second, third, and fourth treatment cycles (Extension Phase); and every 12 weeks during subsequent treatment cycles (Extension Phase). The study-specific procedures include: physical examination, vital signs, 12-lead ECG, performance status, clinical laboratory tests, AEs, concomitant medication and patient compliance. The schedule of assessments is presented in Table 1.

Patients discontinuing study drug will attend an End of Study (EOS) Visit, 4 weeks after the last administration of study drug. In the event that a patient is scheduled to start a new treatment earlier than 3 weeks after the last dose of study drug, the EOS Visit should occur before the start of the new treatment and the reason documented.

Intensive PK sampling will be performed on Days 0 and 28 in all patients enrolled in Stage 1. Sparse PK sampling will be performed on Days 28, 42, and 56 in all patients enrolled in Stage 2.

All patients who withdraw from the study drug, but consent to be followed up for survival status, will be followed up by telephone contact every 3 months, for a maximum of 6 months from the date of last administration of study drug or death, whichever occurs first.

Tumor assessments will be performed at Screening, Days 42 and 84 using the Response Evaluation Criteria in Solid Tumors (RECIST) criteria, version 1.1. Tumor assessments will be performed every 12 weeks during the Extension Phase.

The primary efficacy endpoint is progression-free survival (PFS) rate at 12 weeks, which is defined as the proportion of patients alive and progression-free at Week 12. Patients will be progression-free if they have no evidence of progressive disease (defined according to RECIST guidelines, version 1.1) from the start of treatment to Week 12.

The study uses a two-stage design seeking to detect a true PFS rate of more than 35% in the overall (unselected) population and 40% within the KRAS tumor mutation positive and negative strata. Thirty evaluable patients (15 in each stratum) will be treated initially (Stage 1), with expansion to a maximum of 60 evaluable patients (Stage 2).

An Independent Data Monitoring Committee will act in an advisory capacity to monitor patient safety and efficacy data from the study. The members will be selected on the basis of relevant experience and understanding of clinical research and the issues specific to the therapeutic area, as well as previous data monitoring committee experience. The schedule of blood samples that will be drawn for each patient is presented in Table 2.

TABLE 1

The schedule of assessments.

| Study Procedure | Screening (−42 days) | 1 (0) | 2 (14) | 3 (28) | 4 (42) | 5 (56) | 6 (84) | End of Study (EOS) Visit[2] | Extension Phase[3] |
|---|---|---|---|---|---|---|---|---|---|
| Study visit window (days) | N/A | 0 | ±3 | ±3 | ±3 | ±3 | ±3 | ±7 | ±7 |
| Informed consent[1] | X | | | | | | | | |
| Demographics | X | | | | | | | | |
| Medical & surgical history | X | | | | | | | | |
| Concomitant medication | X | X | X | X | X | X | X | X | X |
| Inclusion/Exclusion criteria | X | | | | | | | | |
| Tumor biomarkers[4] | X | | | | | | | | |
| Physical examination[5] | X | X | X | X | X | X | X | X | X |
| Pregnancy test[6] | X | | | | | | | | |
| Vital signs[7] | X | X | X | X | X | X | X | X | X |
| ECOG performance score | X | X | | X | X | X | X | X | X |
| 12-Lead ECG | X | X | | X | X | X | X | X | X |
| Clinical laboratory tests[8] | X | X | X | X | X | X | X | X | X |
| Tumor assessments[9] | X | | | | X | | X | X | X |
| Dispense study drug[10] | | X | | X | | X | X | | X |
| Drug accountability | | | | X | X | X | X | X | X |
| PK sampling[11] | | X | | X | X | X | | | |
| AE assessment[12] | | X | X | X | X | X | X | X | X |
| Patient compliance | | X | X | X | X | X | X | X | X |

ECOG: Eastern Cooperative Oncology Group; ECG: Electrocardiogram; PK: Pharmacokinetics; AE: Adverse Event; EORTC: European Organization for Research and Treatment of Cancer; QLQ: Quality of Life Questionnaire.
[1] Informed consent must be obtained before the patient undergoes any study-specific procedures.
[2] Patients discontinuing study will attend an EOS Visit, 4 weeks after the last administration of study drug. In the event that a patient is scheduled to start a new treatment earlier than 3 weeks after the last dose of study drug, the EOS Visit should occur before the start of the new treatment and the reason documented. Tumor assessment does not need to be performed at the EOS Visit if this was conducted at the Day 84 Visit. For patients participating in the Extension Phase, the tumor assessment does not need to be performed at the EOS Visit if it has been assessed within 8 weeks of the EOS Visit.
[3] After the first 12-week treatment cycle, patients who are progression-free will be eligible to receive further (12-week) treatment cycles with Compound 1 (Extension Phase), until documented evidence of disease progression, unacceptable toxicity, non-compliance or withdrawal of consent by the patient, or the investigator decides to discontinue treatment, whichever comes first. Investigators should wait at least 7 days after the administration of study drug before initiating alternative treatment is administered. Patients discontinuing the study will attend an EOS Visit 4 weeks after last administration of study drug. Patients will attend visits every 4 weeks (±7 days) during the second, third, and fourth treatment cycles in the Extension Phase. After completion of the fourth treatment cycle, patients will attend visits every 12 weeks (±7 days).
[4] Tumor tissue blocks or slides will be obtained from archival material or from fresh biopsy during the Screening period to determine the tumor KRAS mutation status before the patient is enrolled. A patient may be enrolled based on KRAS test results from the local laboratory. Pleural fluid cytology may be used to determine KRAS mutation status if the cytology was pathologically reviewed and reported to contain malignant cells consistent with NSCLC. Tumor tissue will also be used to study arrays of genomic and proteomic markers of interest.
[5] Weight, height and body mass index (BMI) will be measured at Screening Visit only.
[6] A urine pregnancy test will be performed during the Screening Visit for women of child-bearing potential. This test can be repeated during the study if required by local regulations.
[7] Vital signs (respiratory rate, heart rate, blood pressure, and body temperature) will be performed at each visit. They will be obtained in the sitting position after the patient has rested for 5 minutes. The date and time of the assessment should be recorded.
[8] Hematology, chemistry, and urinalysis. All tests performed at the Central Laboratory Facility.
[9] Radiological and clinical tumor assessments will be performed at Screening, Day 42 and Day 84 using the RECIST criteria version 1.1. Evaluation during Screening must be performed within 14 (±7) days of the date of first administration of study drug. Tumor assessments will be performed every 12 weeks during the Extension Phase.
[10] All Screening procedures and laboratory results must be available and reviewed before the patient receives the first dose of study drug. Study drug should be taken at 8-hour intervals. The time of study drug administration should be recorded in the patient diary.
[11] Intensive PK sampling will be performed on Days 0 and 28 in all patients enrolled in Stage 1. Samples will be taken 30 minutes prior to and 0.5, 1, 2, 3, 4, 6, and 8 hours after the first dose on Day 0, and immediately before and 0.5, 1, 2, 3, 4, 6, and 8 hours after the first dose on Day 28. Sparse PK sampling will be performed on Days 28, 42, and 56 in all patients enrolled in Stage 2. At least two samples will be collected on each occasion, one of which will be a trough concentration (30 minutes prior to dosing and approximately 8 hours after the last dose on the prior day). At least one sample per patient will be timed to coincide with the peak concentration (approximately 3 hours after dosing). The remainder may be taken at any time during the dosing interval.
[12] Patients must be followed for AEs from the date of informed consent until resolution or stabilization, alternative treatment for NSCLC is started, 6 months after last dose of study drug, or loss to follow-up, whichever occurs first. In the event of serious or study drug-related toxicities, the patient will be followed until resolution or stabilization. Safety follow-up data may be collected by telephone contact every 3 months after the EOS Visit.
[13] Day 0 evaluation to be performed before the patient receives the first dose of study drug.
[14] All patients who withdraw from the study drug, but consent to be followed up for survival status, will be followed up by telephone contact every 3 months, for a maximum of 6 months from the date of last administration of study drug or death, whichever occurs first.

TABLE 2

Schedule of Blood Sampling

| Day | Sample No. | Time Schedule (hour) | Time* (hhmm) | Time Window | Activity |
|---|---|---|---|---|---|
| | | Stage 1 | | | |
| 0 | N/A | −1 | 0700 | | Patient registration |
| 0 | N/A | −0.5 | 0730 | | Take blood for laboratory test |
| 0 | 1 | −0.5 | 0730 | | Take pre-dose sample |
| 0 | N/A | −0.25 | 0745 | | Take meal or light snack |
| 0 | N/A | 0 | 0800 | | Take dose |
| 0 | 2 | 0.5 | 0830 | ±5 min | |
| 0 | 3 | 1 | 0900 | ±10 min | |
| 0 | 4 | 2 | 1000 | ±15 min | |
| 0 | 5 | 3 | 1100 | ±20 min | |
| 0 | 6 | 4 | 1200 | ±20 min | |

TABLE 2-continued

Schedule of Blood Sampling

| Day | Sample No. | Time Schedule (hour) | Time* (hhmm) | Time Window | Activity |
|---|---|---|---|---|---|
| 0 | 7 | 6 | 1400 | ±20 min | |
| 0 | 8 | 8 | 1600 | ±20 min | |
| 28 | N/A | −1 | 0700 | | Patient registration |
| 28 | N/A | −0.5 | 0730 | | Take blood for laboratory test |
| 28 | 9 | −0.5** | 0730 | | Take pre-dose sample |
| 28 | N/A | −0.25 | 0745 | | Take meal or light snack |
| 28 | N/A | 0 | 0800 | | Take dose |
| 28 | 10 | 0.5 | 0830 | ±5 min | |
| 28 | 11 | 1 | 0900 | ±10 min | |
| 28 | 12 | 2 | 1000 | ±15 min | |
| 28 | 13 | 3 | 1100 | ±20 min | |
| 28 | 14 | 4 | 1200 | ±20 min | |
| 28 | 15 | 6 | 1400 | ±20 min | |
| 28 | 16 | 8 | 1600 | ±20 min | |
| Stage 2 | | | | | |
| 28 | 1 | −0.5** | N/A | | Trough |
| 28 | 2 | 3 | N/A | ±1 hr | Peak |
| 42 | 3 | −0.5** | N/A | | Trough |
| 42 | 4 | N/A | N/A | | Random*** |
| 56 | 5 | −0.5** | N/A | | Trough |
| 56 | 6 | N/A | N/A | | Random*** |

*Provided for guidance in scheduling the sampling timing for the visits; the time windows must be followed.
**Sample should be taken approximately 8 hours after the prior dose.
***Sample may be taken at any time during the dosing interval Study Procedures
Screening (Up to 42 Days Before Day 0)
Explain the nature of the study and have patients to read and sign an Informed Consent Form (ICF)
Assign patient identifier (Screening number) to patients
Obtain demographic characteristics
Record medical and surgical history including cancer history
Record medication history including cancer treatment history
Screen patients for inclusion/exclusion criteria.
Obtain a tissue sample (tumor biopsy or archived tumor tissue) to determine KRAS tumor mutation status prior to study enrollment. A patient may be enrolled based on KRAS test results from the local laboratory. Pleural fluid cytology may be used to determine KRAS mutation status if the cytology was pathologically reviewed and reported to contain malignant cells consistent with NSCLC. Tumor tissue from patients will also be used to evaluate arrays of genomic and proteomic markers of interest.
Perform physical examinations. Weight, height and body mass index (BMI) will be measured at Screening Visit only
Perform urine pregnancy test for applicable patients only. A urine pregnancy test will be performed during the Screening Visit for women of child-bearing potential. This test can be repeated during the study if required by local regulations
Obtain vital signs. Vital signs (respiratory rate, heart rate, blood pressure, and body temperature) will be obtained in the sitting position after the patient has rested for 5 minutes. The date and time of the assessment should be recorded.
Perform ECOG performance status evaluation
Perform 12-Lead ECG examinations
Perform clinical laboratory tests (hematology, biochemistry, and urinalysis)
Tumor assessments (radiological and clinical tumor assessments). Evaluation at the Screening Visit must be performed within 14 (±7) days of the date of first administration of study drug.
Visit 1 (Day 0)
Record concomitant medications
Perform physical examinations
Obtain vital signs
Perform ECOG performance status evaluation
Perform 12-Lead ECG examinations
Protocol (Compound 1)
Perform clinical laboratory tests (hematology, biochemistry, and urinalysis)
Dispense study drug. All Screening procedures, laboratory results and repeat laboratory results must be available and reviewed before the patient receives the first dose of study drug
Collect pre-dose blood sample within 30 minutes prior to dosing (Stage 1 only)
Administer the first dose of study drug at site and collect PK blood samples 0.5, 1, 2, 3, 4, 6, and 8 hours after dosing (Stage 1 only)
Document study drug dosing time
Record AE and grade possible toxicity
Calculate patient compliance
Perform European Organization for Research and Treatment of Cancer (EORTC) Quality of Life Questionnaires (QLQ)
Visit 2 (Day 14±3)
Record concomitant medications
Perform physical examinations
Obtain vital signs
Perform clinical laboratory tests (hematology, biochemistry, and urinalysis)
Record AE and grade possible toxicity
Calculate patient compliance
Visit 3 (Day 28±3)
Record concomitant medications
Perform physical examinations
Obtain vital signs
Perform ECOG performance status evaluation
Perform 12-Lead ECG examinations
Perform clinical laboratory tests (hematology, biochemistry, and urinalysis)
Dispense study drug
Perform drug accountability
Collect pre-dose blood sample 30 minutes prior to dosing (Stage 1 and 2; approximately 8 hours after the prior dose)
Administer study drug at site and collect PK blood samples 0.5, 1, 2, 3, 4, 6, and 8 hours after dose (Stage 1 only). Stage 2 only: collect PK blood sample 3 hours after dose
Document study drug dosing time
Record AE and grade possible toxicity
Calculate patient compliance
9.1.3.5 Visit 4 (Day 42±3)
Record concomitant medications
Perform physical examinations
Obtain vital signs
Perform ECOG performance status evaluation
Perform 12-Lead ECG examinations
Perform clinical laboratory tests (hematology, biochemistry, and urinalysis)

Tumor assessments (radiological and clinical tumor assessments)
Perform drug accountability
Collect pre-dose blood sample 30 minutes prior to dosing (Stage 2 only; approximately 8 hours after the prior dose)
Administer study drug at site and collect random PK blood sample (Stage 2 only)
Record AE and grade possible toxicity
Calculate patient compliance
Perform EORTC QLQ Visit 5 (Day 56±3)
Record concomitant medications
Perform physical examinations
Obtain vital signs
Perform ECOG performance status evaluation
Perform 12-Lead ECG examinations
Perform clinical laboratory tests (hematology, biochemistry, and urinalysis)
Dispense study drug
Perform drug accountability
Collect pre-dose blood sample 30 minutes prior to dosing (Stage 2 only; approximately 8 hours after the prior dose)
Administer study drug at site and collect random PK blood sample (Stage 2 only)
Record AE and grade possible toxicity
Calculate patient compliance Visit 6 (Day 84±3)
Record concomitant medications
Perform physical examinations
Obtain vital signs
Perform ECOG performance status evaluation
Perform 12-Lead ECG examinations
Perform clinical laboratory tests (hematology, biochemistry, and urinalysis)
Tumor assessments (radiological and clinical tumor assessments)
Dispense study drug
Perform drug accountability
Record AE and grade possible toxicity
Calculate patient compliance
Perform EORTC QLQ End of Study (EOS) Visit (±7 days)
Patients will attend an EOS Visit, 4 weeks after the last administration of study drug. In the event that a patient is scheduled to start a new treatment earlier than 3 weeks after the last dose of study drug, the EOS Visit should occur before the start of the new treatment and the reason documented.
Record concomitant medications
Perform physical examinations
Obtain vital signs
Perform ECOG performance status evaluation
Perform 12-Lead ECG examinations
Perform clinical laboratory tests (hematology, biochemistry, and urinalysis)
Tumor assessments (radiological and clinical tumor assessments). Tumor assessment does not need to be performed at the EOS Visit if this was conducted at the Day 84 Visit. For patients participating in the Extension Phase, the tumor assessment does not need to be performed at the EOS Visit if it has been assessed within 8 weeks of the EOS Visit.
Perform drug accountability
Record AE and grade possible toxicity. Safety follow-up data may be collected by telephone contact every 3 months after the EOS Visit.
Calculate patient compliance
Perform EORTC QLQ
All patients who withdraw from the study drug, but consent to be followed up for survival status, will be followed up by telephone contact every 3 months, for a maximum of 6 months from the date of last administration of study drug or death, whichever occurs first.

Extension Phase Visits (±7 Days)
Patients will attend visits every 4 weeks (±7 days) during the second, third, and fourth treatment cycles. After completion of the fourth treatment cycle, patients will attend visits every 12 weeks (±7 days).
Record concomitant medications
Perform physical examinations
Obtain vital signs
Perform ECOG performance status evaluation
Perform 12-Lead ECG examinations
Perform clinical laboratory tests (hematology, biochemistry, and urinalysis)
Tumor assessments (radiological and clinical tumor assessments)
Dispense study drug
Perform drug accountability
Record AE and grade possible toxicity
Calculate patient compliance
Perform EORTC QLQ Rationale for Single-Arm, Open-Label Phase II Study This is a single-arm, open-label, Phase II study in KRAS-positive and KRAS-negative patients with stage IV (including pleural effusion) non-squamous NSCLC who have failed two lines of anti-cancer therapy. This is defined as patients with radiologically confirmed disease progression following greater than or equal to two, but less than or equal to four, prior lines of systemic anti-cancer therapy. The rationale for this study is described in more detail below.

The subject population of patients with stage IV (including pleural effusion) non-squamous NSCLC who have failed two lines of anti-cancer therapy was chosen for this study as there is a current unmet need to treat this population and results from the first-in-man Phase 1 study indicate that the tumor overall response at the end of treatment showed stable disease for all three patients (one patient in the 200 mg dose group and two patients in the 600 mg dose group) included in the per-protocol set (PPS). The PPS was defined in the Phase 1 study as all patients who completed at least three cycles of treatment with proper imaging assessment (RECIST v.1.1). Furthermore, Compound 1 at 50, 100, 200, 300, 450, and 600 mg dose levels, given daily for 4 weeks, was generally safe and well tolerated, with no particular safety concerns or DLT being identified in the study.

Preclinical data (see Example 2) suggest that patients with KRAS mutation positive tumors may derive greater benefit from Compound 1 therapy. Hence, patients will be stratified according to KRAS mutation status.

An open-label design was selected as this was considered the most suitable design for evaluation of Compound 1 as a single agent in the patient population eligible for participation in this study.

A two-stage, single-arm design was chosen as this was considered most suitable for assessing the safety, tolerability, PK and efficacy of Compound 1 in patients who have previously failed two lines of anti-cancer therapy.

Compound 1 will be administered as a single agent in this study at a dose of 600 mg per day (200 mg t.i.d. administered at 8-hour intervals). This dose regimen was chosen based on results from the Phase 1 clinical study involving NSCLC patients refractory to conventional treatment modalities, which reported good tolerability of Compound 1 up to 600 mg/day. The area under the plasma concentration-time curve from 0 to 24 hours ($AUC_{0-24}$) after single dose administration on Day 1 of the first treatment cycle (Cycle 1) increased by 18.79%, 200.1%, 215.16%, 265.19% and 396.61% at the 100, 200, 300, 450, and 600 mg dose levels, respectively, when compared with the 50 mg dose level; whereas on Day 28 of Cycle 1, the $AUC_{0-24}$ decreased by 34.88% at the 100 mg dose level and increased by 133.58%, 141.87%, 680.65% and 562.54% at the 200, 300, 450, and 600 mg dose levels, respectively. Thus, the $AUC_{0-24}$ was not linearly proportional to the Compound 1 dose on Day 1 and Day 28. There were no significant differences in $AUC_{0-24}$ in the 100-300 mg dose range on Day 1 and Day 28. The highest peak concentration ($C_{max}$) over the 100-300 mg dose range was observed with the 200 mg dose on Day 28. One patient in the 200 mg dose group and two patients in the 600 mg dose group exhibited stable disease at the end of treatment.

Thus, in order to maintain a high drug concentration and enhance the efficacy of Compound 1 200 mg t.i.d. (every eight hours) has been chosen as the dosage regimen for this study.

The study design is based on the assumption that within each of the KRAS tumor mutation positive and negative strata, a PFS rate at 12 weeks of 40% and 35% overall would be of interest. Further testing would not be pursued if the PFS rate at 12 weeks was less than 15%.

The study drug will be administered until disease progression, occurrence of unacceptable toxicity, non-compliance or withdrawal of consent by the patient, or investigator decision to stop study drug, whichever comes first.

Appropriateness of Measurements

The primary efficacy endpoint in this study is the PFS rate, defined as the proportion of patients alive and progression-free at Week 12. Patients will be progression-free if they have no evidence of progressive disease (per RECIST version 1.1) from the start of treatment to Week 12. The RECIST guidelines recognize that the proportion progression-free at a pre-specified time point is an appropriate to assess the anti-tumor activity of agents such as Compound 1, where biological activity is more likely to translate into stabilization of disease.

Tumor response, based on radiological measurement, is a standard and well accepted efficacy endpoint in clinical development. Response to study drug will be assessed in this study using RECIST version 1.1, an internationally standardized and widely accepted standard for measuring response to treatment in cancer.

The secondary efficacy measures of objective response rate (ORR), disease control rate (DCR), duration of overall tumor response (DR), PFS, overall survival (OS) and time to progression (TTP) are also well accepted efficacy endpoints in clinical development for oncology studies and in line with recommendations in the European Medicine's Agency (EMA), Committee for Medicinal Products for Human Use (CHMP) Guideline on the Evaluation of Anticancer Medicinal Products in Man (EMA/CPMP/205/95/Rev.4, 2012)[26]; and the United States (US) Food and Drug Administration (FDA) Guidance for Industry on Clinical Trial Endpoints for the Approval of Cancer Drugs and Biologics (US Department of Health and Human Services, May 2007).

The safety and PK endpoints in this study are standard and well understood endpoints in clinical oncology. The corrected QT (QTc) assessment strategy for this study is based on recommendations in the International Conference on Harmonisation (ICH) E14 guideline[28] and is designed to focus on the collection of cardiac safety information. There are no concerns for cardiotoxicity based on the mechanism of action, the nonclinical toxicology studies, or the limited clinical information available to date. Twelve-lead ECGs are required during Screening, during treatment, and at the End of Treatment Visit, and as clinically indicated.

Quality of life will be assessed using EORTC QLQ C30 (QLQ-C30) and the Module on Lung Cancer (QLQ-LC13), which is a validated instrument for assessing quality of life (QoL) in patients with lung cancer.

The EORTC QLQ-$C_{30}$/EORTC QLQ-LC13 is comprised of a global health status scale, five functional scales (physical, role, emotional, cognitive, and social), three symptom scales (fatigue, nausea and vomiting, and pain), and several single items, as well as a module designed specifically for lung cancer. These QoL assessment tools are included in this study in order to evaluate the side effects of Compound 1 as well as the impact of treatment on patients' disease-related symptoms.

Risk/Benefit and Ethical Assessment:

No fatal or severe/serious adverse drug reaction has been reported by the marketed product (food supplement) of *Antrodia camphorata*. Patients anticipated to be enrolled into the study will be non-squamous NSCLC patients with confirmed disease progression following two prior lines of systemic anti-cancer therapy for recurrent/metastatic disease (one of which should be a platinum-based regimen). As the dose utilized for this study is considered conservative and acceptable, and the patients targeted are mainly patients with rather limited treatment options, the risk and benefit assessment is deemed justifiable.

Selection of Study Population

Inclusion Criteria:

Patients eligible for enrollment in the study must meet all of the following criteria:

1. Cytologically or histologically confirmed non-squamous NSCLC Stage IV (including pleural effusion)
2. Radiologically confirmed disease progression following greater than or equal to two, but less than or equal to four, prior lines of systemic anti-cancer therapy, one of which should be a platinum-based regimen, OR the patient has refused treatment with approved treatment modalities, OR the investigator feels that the patient is not a candidate for other systemic therapy. Patients with epidermal growth factor receptor (EGFR)-positive mutations should have been offered treatment with an EGFR-TK inhibitor prior to enrolment in this study. Adjuvant therapy with or without maintenance therapy would count as one line of systemic therapy. A line of therapy requires at least two 3-4 week complete cycles unless it was stopped due to toxicity, in which case it would count as one line of therapy
3. At least one radiologically measurable target lesion per RECIST version 1.1
4. Fresh or archival biopsy tissue available to determine KRAS tumor mutation status
5. At least 18 years of age at the time of signing informed consent
6. Life expectancy of at least 3 months
7. Written informed consent that is consistent with ICH Tripartite Guideline on Good Clinical Practice (GCP) guidelines 8. Patient or legally acceptable representative has granted written informed consent before any study-specific procedures (including special Screening tests) are performed
9. Eastern Cooperative Oncology Group (ECOG) performance score of 0, 1 or 2 Protocol (Compound 1)
10. Hemoglobin ? 9.0 g/dL; platelets ? 100×10⁹/L; ANC ? 1.5×10⁹/L without the use of hematopoietic growth factors
11. Bilirubin and creatinine less than 2×upper limit of normal (ULN) for the institution
12. Albumin ? 2.5 mg/dL
13. Aspartate aminotransferase (AST) and alanine aminotransferase (ALT) less than 5×ULN for the institution
14. Prothrombin time less than 1.5×ULN for the institution
15. Potassium, magnesium and phosphorus within the normal range for the institution (supplementation is permissible)
16. Willing to use two medically accepted and effective methods of contraception from the list below during the study (both men and women as appropriate) and for 3 months after the last dose of study drug:
   Established use of oral, injected or implanted hormonal methods of contraception.
   Placement of an intrauterine device or intrauterine system.
   Barrier methods of contraception: Condom or Occlusive cap (diaphragm or cervical/vault caps) with spermicidal foam/gel/film/cream/suppository.
   Male sterilization (with the appropriate post-vasectomy documentation of the absence of sperm in the ejaculate).
   True abstinence: When this is in line with the preferred and usual lifestyle of the patient.
17. Recovery to ∼ Grade 1 or baseline of any toxicities due to prior treatments, excluding alopecia Exclusion Criteria Patients meeting any of the following criteria must not be enrolled in the study:
1. Chemo-, hormone- or immunotherapy, within 4 weeks or within less than four half-lives of the date of first administration of study drug and/or persistence of toxicities of prior anti-cancer therapies which are deemed to be clinically relevant
2. Radiotherapy within the past 2 weeks prior to the date of first administration of study drug.
3. Previous treatment with a histone deacetylase (HDAC) inhibitor or an EGFR inhibitor within at least 4 weeks of the date of first administration of study drug
4. Treatment with any drug(s) known to be a strong inhibitor or inducer of CYP2C19, CYP3A4, CYP2C8, and CYP2E1, within 14 days of the date of first administration of study drug
5. Brain metastases which are symptomatic; patients with treated brain metastases are eligible with stable brain disease for at least 4 weeks without the requirement for steroids or anti-epileptic therapy
6. Inability to swallow oral medications or a recent acute gastrointestinal disorder with diarrhea e.g., Crohn's disease, malabsorption, or Common Terminology Criteria for Adverse Events (CTCAE) Grade>2 diarrhea of any etiology at baseline
7. Other malignancies diagnosed within the past 5 years (other than curatively treated cervical cancer in situ, non-melanoma skin cancer, superficial bladder tumors Ta [non-invasive tumor] and TIS [carcinoma in situ], or non-metastatic prostate cancer stage 1 to 2, which has been previously treated with surgery or radiation therapy, and serum prostate-specific antigen is within normal limits [test performed within the past 12 months prior to the date of first administration of study drug])
8. Patients with any serious active infection (i.e., requiring an intravenous antibiotic, antifungal, or antiviral agent)
9. Patients with known HIV, active hepatitis B or active hepatitis C
10. Patients who have any other life-threatening illness or organ system dysfunction, which in the opinion of the investigator, would either compromise patient safety or interfere with the evaluation of the safety of the study drug
11. Known or suspected substance abuse or alcohol abuse
12. Women of child-bearing potential or men who are able to father a child unwilling to use two medically accepted and effective methods of contraception during the study (as specified in the inclusion criteria)
13. Pregnancy or breast feeding
14. Patient unable to comply with the protocol
15. History of clinically significant or uncontrolled cardiac disease, including congestive heart failure, angina, myocardial infarction, arrhythmia, including New York Heart Association functional classification of 3

Treatment of Patients

Study Drug Treatment and Dosing:

Compound 1 should be taken every 8 hours approximately 15 minutes after a meal or light snack and not within ±1 hour of drinking an ethanol-containing beverage e.g. an alcoholic drink. Subjects who forget or are unable to take a dose at the scheduled time should be instructed to take the dose as soon as possible. If they do not remember or are unable to take the dose prior to the next scheduled dose, they should take the scheduled dose and the missed dose will not be made up. The date and time of each study drug administration should be recorded in the patient diary.

Treatment for Study Drug Overdose:

Treatment of study drug overdose is at the discretion of the investigator.

Administration on Pharmacokinetic Sampling Days

On the days in Stage 1 when PK sampling will be performed, namely, Days 0 and 28, patients will eat a meal at the study site and then take their next dose of Compound 1 15 minutes (±3 minutes) after completion. Patients should take their last dose of Compound 1 on Day 27, approximately 8 hours before the scheduled time of dosing at the study site.

Study drug should be taken at 8-hour intervals, approximately 15 minutes after a meal or light snack, and not within ±1 hour of drinking an ethanol-containing beverage, e.g. an alcoholic drink. The exact time of study drug administration should be recorded in the patient diary. All capsules must be swallowed within 2 to 3 minutes. On Days 0 and 28 patients will remain at the site for 8 hours after study drug administration if required for PK.

On days of PK sampling in Stage 2, namely, Days 28, 42, and 56, patients will eat a meal at the study site and then take their next dose of Compound 1 15 minutes (±3 minutes) after completion. Patients should take their last dose of Compound 1 on Days 27, 41, and 55 approximately 8 hours before the scheduled time of dosing at the study site.

Extension Phase

After the first 12-week treatment cycle, patients who are progression-free will be eligible to receive further (12-week) treatment cycles with Compound 1 in the Extension Phase.

Patients participating in the Extension Phase will follow a schedule similar to that of the first 12-week treatment cycle, except no PK samples will be drawn. Patients will attend visits every 4 weeks (±7 days) during the second, third, and fourth treatment cycles. After completion of the fourth treatment cycle, patients will attend visits every 12 weeks (±7 days).

Patients may continue in the Extension Phase until documented evidence of disease progression, unacceptable toxicity, non-compliance or withdrawal of consent by the patient, or the investigator decides to discontinue treatment, whichever comes first.

If there is Grade 3 or 4 toxicity, the patient's dose will drop down to the next lower dose according to the Dose Modification and Toxicity Management Guidelines as follows.

Dose Modification

The guidelines for dose modification and management of drug toxicity are as follows:

TABLE 3

Dose Modification and Management of Drug Toxicity Guidelines

| Event | Grade | Management/Action |
|---|---|---|
| All non-hematologic and hematologic adverse events that are study drug-related | 1 or 2<br>3<br>4 | No change.<br>Suspend treatment. Treatment may resume if toxicity is resolved to grade ≤1 or returns to baseline within 7 days. Treatment should resume at a reduced dose (100 mg t.i.d). If toxicity lasts more than 7 days, study drug will be permanently discontinued (subject to investigator and Medical Monitor agreement); if a patient experiences another grade ≥3 toxicity at the reduced dose, then study drug will be permanently discontinued. |

Treatment may be withheld for up to 7 days due to study drug-related toxicities. Patients will be permanently discontinued from the study drug if treatment interruption is more than 7 days and the investigator and Medical Monitor consider that permanent cessation of study drug is necessary. If a patient resumes treatment before the end of a cycle, the patient will have to complete the rest of the treatment of that cycle.

When patients are suspected to experience Grade 3 or more AEs, they should contact the site as soon as possible for an appointment and bring back any unused study drug to the site. Treatment should only be withheld for nausea, vomiting, and diarrhea of Grade≥3 if symptoms remain at Grade≥3 despite adequate treatment. If dose modification is deemed necessary, the unused study drug will be retrieved and a new bottle with quantity of study drugs calculated based on the modified dose will be dispensed. Sufficient study drug should be dispensed for the period from the day of dose modification to the next dispensing visit.

The quantity given will be recorded in the eCRF and the drug accountability log. At the time the patient returns the unused study drug, they will be counted at the site and recorded in the eCRF. The dates and durations of any dosing interruptions will be recorded in the eCRF.

Assessment of Efficacy

The primary and secondary efficacy analyses will be based on the independent centralized assessment of medical images. A detailed description of the process is provided in the Independent Review Charter.

Efficacy Variables

Primary Endpoint:

The primary endpoint is the PFS rate at 12 weeks, defined as the proportion of patients alive and progression-free at Week 12. Patients will be progression-free if they have no evidence of progressive disease (defined according to RECIST guidelines, version 1.1) from the start of treatment to Week 12.

Tumor response will be assessed at 6-week intervals during the first treatment cycle using the RECIST criteria version 1.1. Each patient will be assigned one of the following categories: 1) complete response (CR), 2) partial response (PR), 3) stable disease (SD), or 4) progressive disease (PD). Patients who died from any cause or discontinued the study for any reason without a post-screening or Week 12 tumor assessment will be considered as failing to respond to treatment.

Secondary Efficacy Endpoints:

Secondary efficacy endpoints are as follows:

Objective response rate, defined as the proportion of patients whose best overall response is either CR or PR according to RECIST version 1.1. The best overall response is the best response recorded during the first 12-week treatment cycle.

Disease control rate, defined as the proportion of patients with a documented CR, PR and SD during the first 12-week treatment cycle according to RECIST version 1.1.

Duration of overall tumor response, defined as the interval between the date of the first observation of tumor response (CR or PR) and the date of disease progression or death.

Progression free survival, defined as the time from the date of first administration of study drug to objective tumor progression by RECIST version 1.1 or death due to any cause, whichever occurs first.

Overall survival, defined as the time from the date of first administration of study drug to death from any cause.

Time to progression, defined as the time from the date of first administration of study drug to objective tumor progression by RECIST version 1.1.

Patient Reported Outcome Endpoint:

The PRO endpoint is as follows: European Organization for Research and Treatment of Cancer QLQ-C30 and the EORTC QLQ-LC13.

Pharmacokinetic Endpoints:

For Stage 1, PK endpoints will be derived for intensively sampled PK profiles by non-compartmental methods and include:

$C_{max}$: peak concentration
$C_{trough}$: trough plasma concentration
$T_{max}$: peak time
$AUC_\tau$: area under the plasma concentration-time curve over the 8-hour dosing interval
$T_{1/2}$ terminal half-life
Vz/F: apparent volume of distribution during elimination
CL/F: apparent oral clearance
$T\frac{1}{2},_{eff}$: effective half-life If possible, PK data from all patients will be analyzed using PopPK methods and post hoc estimates of Compound 1 exposure (i.e., $C_{max}$, $C_{trough}$, and $AUC_\tau$) will be computed for exploration of potential exposure-response relationships.

Tumor Biomarkers:

Subgroup analyses will assess the predictive value of tumor biomarkers.

Efficacy Assessments

Tumor Measurement:

Tumor assessment will be performed during the 12 week treatment period using computed tomography (CT) scan or magnetic resonance imaging (MRI) according to RECIST guideline, version 1.1 at the Screening Visit, Visit 4 (42), and Visit 6 (84). Tumor assessments will be performed every 12 weeks during the Extension Phase. The tumor assessment does not need to be performed at the EOS Visit if this was conducted at the Day 84 Visit. For patients participating in the Extension Phase, the tumor assessment does not need to be performed at the EOS Visit if it has been assessed within 8 weeks of the EOS Visit. The preferred scan is a CT of the chest, abdomen, and pelvis, performed with IV contrast. If patients have a contraindication to iodinated contrast, such as a documented allergy or impaired renal function, a non-contrast CT of the chest and MM of the abdomen and pelvis is permitted (MRI preferably with gadolinium contrast, though this may be omitted if renal impairment is severe). Imaging evaluation at the Screening Visit must be performed within 14 (±7) days of the date of first administration of study drug. The same method of assessment will be used at each tumor assessment visit as used at the baseline visit.

Clinical Response—Solid Tumors:

Clinical response will be evaluated according to RECIST criteria in evaluable patients, by comparing the measurements and number of target lesions at baseline and during the study.

Tumor Biomarkers:

Formalin fixed paraffin embedded (FFPE) tumor tissue will be submitted for analysis of tumor biomarkers. Next-generation sequencing will be used to screen a panel of 236 genes commonly mutated in tumors, including KRAS, EGFR, and ALK. Patients will be stratified according to KRAS mutation status to test for possible differences in sensitivity/resistance to the study drug. In addition, selected samples may also have ALK and ROS1 status determined by immunohistochemistry. Refer to the Laboratory Manual for details of the mutation assays, and instructions for sample collection, handling, and shipment.

Pharmacokinetics

Pharmacokinetic Sampling

PK sampling will be performed on Day 0 and Day 28 in all patients enrolled in Stage 1 at the following time points:

Day 0: (Approximately 5 mL per sample, 60 mL in total) 30 minutes prior to and 0.5, 1, 2, 3, 4, 6, and 8 hours after the first dose.

Day 28: (Approximately 5 mL per sample, 60 mL in total) immediately before and 0.5, 1, 2, 3, 4, 6, and 8 hours after the first dose on Day 28.

Sparse PK sampling will be performed on Days 28, 42, and 56 in all patients enrolled in Stage 2. At least two samples will be collected on each occasion, one of which will be a trough concentration (30 minutes prior to the first dose on Days 28, 42, and 56 and approximately 8 hours after the last dose on the prior day). At least one sample per patient will be timed to coincide with the peak concentration (3 hours after the first dose). The remainder may be taken at any time during the dosing interval.

Each blood sample will be analyzed for Compound 1 plasma concentration to determine PK parameters after administration of Compound 1 using a fully validated bioanalytical method (a copy of the analytical method validation report and bioanalytical report will be included in the clinical study report).

Pharmacokinetic Sampling Procedures

Blood Samples:

Samples of venous blood will be obtained in 5 mL sodium heparin Vacutainer® tubes at the sample times listed above. Immediately after collection the tube will be gently inverted 8 to 10 times to mix the anticoagulant with the blood sample. All samples will be processed and placed into a freezer within one (1) hour after collection. The plasma fraction will be separated by placing the collection tube into a refrigerated centrifuge (4° C.) for 10 minutes at 3000 rpm. The plasma fraction will be withdrawn by pipette and divided into two polypropylene freezing tubes (with each tube receiving approximately equal aliquots). All sample collection and freezing tubes will be clearly labeled with the patient number, the study period, and the collection time. Labels will be fixed to freezing tubes in a manner that will prevent the label from becoming detached after freezing. All plasma samples will be placed into a freezer at −70° C. within 1 hour after collection.

Analytical Methodology:

The concentration of study drug will be determined from the plasma samples using a validated analytical method. Details of the method validation and sample analysis will be included in the final clinical study report.

Assessment of Safety:

Safety will be assessed based on AEs, clinical laboratory results (routine hematology and biochemistry), physical examination, vital signs, and ECG recording.

Eastern Cooperative Oncology Group Performance Status

The performance status of patients will be graded by their ECOG performance status score at every visit, except Visit 2. The description of ECOG performance status scale is defined as follows:

- 0: Normal activity. Fully active, able to carry on all pre-disease performance without restriction.
- 1: Symptoms, but ambulatory. Restricted in physically strenuous activity, but ambulatory and able to carry out work of a light or sedentary nature (e.g., light housework, office work).
- 2: In bed<50% of the time. Ambulatory and capable of all self-care, but unable to carry out any work activities. Up and about more than 50% of waking hours.
- 3: In bed>50% of the time. Capable of only limited self-care, confined to bed or chair more than 50% of waking hours.
- 4: 100% bedridden. Completely disabled. Cannot carry on any self-care. Totally confined to bed or chair.
- 5: Dead.

Statistical Evaluation

Sample Size and Power:

The study uses a two-stage design. Thirty evaluable patients (15 in each stratum) will be treated initially (Stage 1), with expansion to a maximum of 60 evaluable patients (Stage 2). Enrollment will continue until the target number of evaluable patients has been enrolled.

It is assumed that within each of the KRAS tumor mutation positive and negative strata, a PFS rate at 12 weeks of 40% and 35% overall (unselected) population will be of interest. Further testing will not be pursued if the PFS rate at 12 weeks is less than 15%.

Initially, 15 evaluable patients are to be accrued within each stratum. If two or more patients are alive and progression-free at Week 12 within a stratum, then an additional 15 evaluable patients will be accrued to that stratum for a total of 30 evaluable patients. If nine or more patients are alive and progression-free at Week 12 within the 30 evaluable patients in the stratum then Compound 1 will be considered worthy of further study in that cohort. This design will allow a significance level of 2.8% and a power of 90.5% within each stratum.

In addition to within-stratum hypothesis testing, this study is also designed to investigate the PFS rate at 12 weeks in the overall (unselected) population. If less than three patients are alive and progression-free at Week 12 in the first 20 evaluable patients, and the criterion for continuing the individual stratum are not met, then the accrual for all strata will be discontinued. Otherwise, a maximum of 40 additional evaluable patients will be entered (depending on whether any individual stratum is closed). Fifteen or more patients alive and progression-free at Week 12 out of the maximum 60 evaluable patients would warrant further study. The overall design has a significance level of 2.8% (probability of falsely declaring the regimen with a 15% PFS rate at 12 weeks to warrant further study) and power 95.6% (probability of declaring the regimen with a 35% PFS rate at 12 weeks in the overall population to warrant further study).

Statistical Methods:

All analysis will be performed in accordance with a detailed Statistical Analysis Plan (SAP).

Analysis Populations

The primary analysis will be performed on the evaluable population. The evaluable population will consist of all enrolled patients who receive at least one dose of Compound 1 and have a valid baseline tumor assessment. A valid baseline assessment is defined as a readable scan (one in which the images are of high enough quality to permit accurate assessment of the tumor) performed within 14 (±7) days of the date of first administration of study drug. For the efficacy analysis, enrollment will continue until the target number of evaluable patients has been enrolled. The full analysis set (FAS) and PPS will be used for supportive efficacy analyses. The FAS will consist of patients in the evaluable population who have at least one post-baseline tumor assessment. The PPS will consist of patients in the FAS who do not have major protocol violations.

The PK population will consist of patients in the first stage who have an evaluable PK profile, defined as a profile from which at least one of the PK parameters stated as endpoints can be estimated, and no protocol deviations that would affect the PK of Compound 1.

The PopPK population will consist of patients with at least two plasma concentrations and sufficient and reliable dosing histories.

The Safety population will comprise all patients who are treated with at least one dose of study drug. The PRO population will consist of all patients who have completed the QoL Questionnaire on Day 0 and on at least one occasion after the first administration of study drug.

Efficacy Analysis:

Except for the primary efficacy analysis, there will be no formal statistical testing. All data will be summarized and listed as appropriate. All efficacy endpoints will be evaluated in both the overall (unselected) population and within-stratum. The primary and secondary efficacy analyses will be based on the independent centralized assessment of medical images.

Primary Efficacy Analysis:

The primary endpoint is the PFS rate at 12 weeks, defined as the proportion of patients alive and progression-free at Week 12. Patients will be progression-free if they have no evidence of progressive disease (defined according to RECIST guideline, version 1.1) from the start of treatment to Week 12. An evaluable patient who died from any cause or discontinued the study for any reason without a post-screening or Week 12 tumor assessment will be considered as failing to respond to treatment.

Secondary Efficacy Analysis:

The FAS and PPS will be used for the secondary efficacy analyses. The secondary efficacy endpoints comprise the following: ORR, DCR, DR, PFS, OS and TTP. The ORR is defined as the proportion of patients whose best overall response is either CR or PR according to RECIST version 1.1. The best overall response is the best response recorded during the first 12-week treatment cycle. The DCR is defined as the proportion of patients with a documented CR, PR and SD during the first 12-week treatment cycle according to the RECIST version 1.1. For both ORR and DCR, 95% two-sided CIs will be presented. The DR is defined as the interval between the date of the first observation of tumor response (CR or PR) and the date of disease progression or death. The DR will be summarized using Kaplan-Meier methods and displayed graphically where appropriate. The DR will be calculated for the subgroup of patients with tumor response (CR or PR). If the number of patients with a documented CR or PR is small then only descriptive statistics or listings will be presented.

Progression-free survival is defined as the time from the date of first administration of study drug to objective tumor progression by RECIST version 1.1 or death due to any cause, whichever occurs first. The censoring rule for PFS will be described in the SAP.

Overall survival is defined as the time from the date of first administration of study drug to death from any cause. The censoring rule for OS will be described in the SAP.

Time to progression is defined as the time from the date of first administration of study drug to objective tumor progression by RECIST version 1.1. The censoring rule for TTP will be described in the SAP. Objective response rate and DCR will be reported with category counts, percentage and 95% CIs. PFS, OS and TTP will be evaluated using Kaplan-Meier estimates and curves will be generated based on these estimates. Time-to-event endpoints will be re-analyzed when all patients have completed the Extension Phase.

Pharmacokinetic Analysis:

Non-compartmental PK analysis will be performed for the PK population, which will consist of patients in the first stage who have an evaluable PK profile, defined as a profile from which at least one of the PK parameters stated as endpoints can be estimated and no protocol deviations that would affect the PK of Compound 1. Curves of Compound 1 concentration versus time in plasma will be constructed for each patient. Descriptive statistics will be presented for all PK parameters.

The following PK parameters will be estimated by non-compartmental methods:

$C_{max}$: peak concentration
$C_{trough}$: trough plasma concentration
$T_{max}$: peak time
$AUC_T$: area under the plasma concentration-time curve over the 8-hour dosing interval
$T\frac{1}{2}$: terminal half-life
Vz/F: apparent volume of distribution during elimination
CL/F: apparent oral clearance
$T\frac{1}{2}_{,eff}$: effective half-life Full details of the PK analysis will be provided in the SAP.

If possible, PK data from all patients in the PopPK population will be analyzed using PopPK methods and post hoc estimates of Compound 1 exposure computed for exploration of potential exposure-response relationships. Full details of the PopPK analysis will be provided in a separate modeling and simulation analysis plan (MSAP).

Interim Analysis:

An interim analysis for safety and efficacy will be performed when 20 patients overall and when 15 patients within each stratum are evaluable for the primary endpoint, PFS rate at 12 weeks. If less than two patients are alive and progression-free within a stratum, then the accrual for that stratum will be discontinued. Otherwise, a maximum of 15 additional evaluable patients will be accrued to that stratum for a total of 30 evaluable patients. Furthermore, if less than three patients in the overall (unselected) population are alive and progression-free in the first 20 evaluable patients, and the criterion for continuing the individual stratum are not met, then the accrual for all strata will be discontinued. Otherwise, a maximum of 40 additional evaluable patients will be entered (depending on whether any individual stratum is closed).

Tumor Biomarkers:

Tumor tissue blocks or slides will be obtained from archival material or from fresh biopsy during the Screening period to determine the KRAS tumor mutation status before enrolling the patient into the study. A patient may be enrolled based on KRAS test results from the local laboratory. Pleural fluid cytology may be used to determine KRAS mutation status if the cytology was pathologically reviewed and reported to contain malignant cells consistent with NSCLC. Patients will be stratified according to KRAS mutation status to test for possible differences in sensitivity/resistance to the study drug. KRAS and other tumor biomarkers will be used in subgroup analyses to determine the molecular signature of patients who could benefit from Compound 1. To that effect, tumor tissue from patients will be used to evaluate arrays of genomic and proteomic markers of interest.

Study Results:

23 subjects had been enrolled and met the criteria of Safety Population. 22 subjects met the criteria of Evaluable Population based on the independent assessment. 18 subjects met the criteria of Full Analysis set where 4 subjects in evaluable population do not have post baseline tumor assessment. 4 subjects out of 20 are alive or progression free at 12 week after taking Compound 1.

It is surprisingly found that in KRAS mutant patients, the tumor progression free rate or the proportion of patients alive at 12 weeks was 3/14. It is noted that all patients in this study are patients with stage IV (including Pleural Effusion) non-squamous non-small cell lung cancer (NSCLC) who have failed two lines of anti-cancer therapy.

Compound 1 exhibited 5/11 efficacy for target and non-target lesions at lung related sites. Previous study on tissue distribution of Compound 1 in rat indicated that the highest Compound 1 accumulation was found in lung tissue. This preliminary phase 2 result shows a positive correlation between the efficacy and the concentration of Compound 1 in lung tissue.

Thus, unexpectedly, according to the preliminary clinical results of Compound 1 in NSCLC patients, Compound 1 provides therapeutic benefits for NSCLC patients with Stage IV, especially patients with KRAS mutation.

Example 5: Oral Formulation

To prepare a pharmaceutical composition for oral delivery, 200 mg of an exemplary Compound 1 was mixed with 200 mg of corn oil. The mixture was incorporated into an oral dosage unit in a capsule, which is suitable for oral administration.

In some instances, 200 mg of a compound described herein is mixed with suitable amount of starch. The mixture is incorporated into an oral dosage unit for, such as a hard gelatin capsule, which is suitable for oral administration.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for the treatment of an individual with advanced stage lung cancer comprising (1) selecting for treatment an individual who has advanced stage lung cancer and is KRAS positive and (2) administering to said individual a therapeutically effective amount of a cyclohexenone compound having the structure:

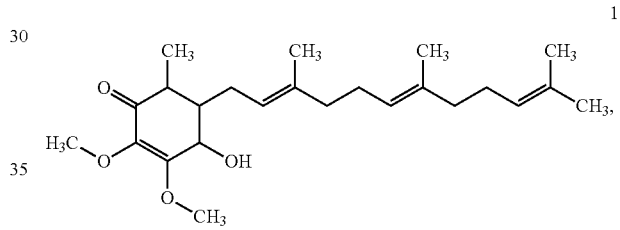

or a pharmaceutically acceptable salt, or solvate thereof, wherein said individual failed at least two lines of anti-cancer therapy.

2. The method of claim 1, wherein said advanced stage lung cancer is non-small cell lung cancer stage IV.

3. The method of claim 1, wherein said method improves or maintains the quality of life of said individual diagnosed with non-small cell lung cancer stage IV.

4. The method of claim 1, wherein said cyclohexenone compound, or a pharmaceutically acceptable salt or solvate thereof, is administered parenterally, intravenously, orally, or by injection.

5. The method of claim 4, wherein the dose of said cyclohexenone compound is about 600 mg per day.

6. The method of claim 1, wherein said compound is isolated from *Antrodia camphorata*.

7. The method of claim 3, wherein said cyclohexenone compound, or a pharmaceutically acceptable salt or solvate thereof, is administered parenterally, intravenously, orally, or by injection.

8. The method of claim 4, wherein the dose of said cyclohexenone compound is about 50-450 mg per day.

9. The method of claim 3, wherein said compound is isolated from *Antrodia camphorata*.

* * * * *